United States Patent [19]

Jacobson

[11] Patent Number: 6,004,257

[45] Date of Patent: Dec. 21, 1999

[54] METHOD FOR AMELIORATING THE AGING PROCESS AND THE EFFECTS THEREOF UTILIZING ELECTROMAGNETIC ENERGY

[76] Inventor: Jerry I. Jacobson, 2006 Mainsail Cir., Jupiter, Fla. 33477-1418

[21] Appl. No.: 08/440,896

[22] Filed: May 24, 1995

Related U.S. Application Data

[63] Continuation-in-part of application No. 08/249,244, May 25, 1994, abandoned.

[51] Int. Cl.$^6$ ........................................................ A61N 2/00
[52] U.S. Cl. ................................................................ 600/9
[58] Field of Search ............................................. 600/9–15

[56] References Cited

U.S. PATENT DOCUMENTS

| | | | |
|---|---|---|---|
| 5,269,746 | 12/1993 | Jacobson | 600/13 |
| 5,366,435 | 11/1994 | Jacobson | 600/13 |

FOREIGN PATENT DOCUMENTS

| | | | |
|---|---|---|---|
| 45680/89 | 9/1993 | Australia | A61N 1/42 |
| 0 371 504 A2 | 6/1990 | European Pat. Off. | A61N 2/04 |

OTHER PUBLICATIONS

Eichhorn, Gunther L., Aging Genetics and the Environment: Potential of Errors Introduced into Genetic Information Transfer by Metal Ions, *Mechanisms of Ageing and Development*, 9 (1979), pp. 291–301.

Jacobson, Jerry I., The Question of Ameliorating the Aging Process, Even Macula Regeneration with Magnetic Fields, *Panminerva Medica* (1991), vol. 33 (4), pp. 205–208.

Jacobson, Jerry I.,Jacobson Resonance: The Coupling Mechanism for Weak Electromagnetic Field Bioeffects, and a New Way to Approach Magneto Therapy, *Panminerva Medica*, vol. 36, No. 1 (Mar. 1994), pp. 34–41.

Jacobson, Jerry I. and Yamanashi, William S., A Possible Physical Mechanism in the Treatment of Neurologic Disorders with Externally Applied Pico Iesla Magnetic Fields, *Physiol., Chem., Phys. & Med.* NMR (1994), vol. 26, pp. 287–297.

Jacobson, Jerry I., Is the Fusion Process the Basis for Growth, Repair and Aging?, *Minerva Medica*, vol. 32, No. 3 (Jul.–Sep. 1990), pp. 132–140.

Jacobson, Jerry I., Jacobson Resonance is the Basis From Which to Evaluate Potential Hazard and Therapeutic Benefit from Extrinsic Magnetic Fields, *Minerva Medica*, vol. 35, No. 3 (Sep. 1993), pp. 138–148.

*Primary Examiner*—John P. Lacyk
*Attorney, Agent, or Firm*—Ruden, McClosky, Smith, Schuster & Russell, PA

[57] ABSTRACT

A method and apparatus for ameliorating the aging process and the effects of aging and maintaining the integrity of health is provided. The method includes subjecting biological systems to alternating and steady magnetic fields having flux densities ranging from $10^{-6}$ gauss to $10^{-20}$ gauss and frequencies from 0 Hertz to $10^{14}$ Hertz. The calculation is made with reference to the equation $mc^2=Bvlq$, where m=mass; c=speed of light; B=magnetic flux density; v=inertial velocity of the mass contained in l; l=length of the conductive body; q=unity. The process begins by targeting the larger targets first and then diminishing the field magnitude slowly and incrementally according to the targets. The frequency when AC is indicated is calculated with the cyclotron resonance formula, $f_c=qB/(2\pi m)$. The apparatus includes a specially constructed pool or tub for generating the specific magnetic flux necessary for treatment. Orientation of the patient with reference to North, South, East and West is varied. The earth's position in relation to the sun is taken into account. The patient may be in an upright, prone or swimming position depending on the specific treatment scheme.

19 Claims, 7 Drawing Sheets

METHOD FOR AMELIORATING THE AGING PROCESS AND THE EFFECTS THEREOF UTILIZING ELECTROMAGNETIC ENERGY

CROSS REFERENCES TO RELATED APPLICATIONS

This is a continuation in part of application Ser. No. 08/249,244 filed May 5, 1994 abn.

TECHNICAL FIELD

This invention relates to applying electromagnetic energy to living tissues for ameliorating the aging process and the effects thereof and maintaining the integrity of health, and in particular, to applying a specific magnetic flux density and frequency of electromagnetic radiation calculated from the mass of the targeted tissues, with a specific patient orientation for a given amount of time.

BACKGROUND OF THE INVENTION

Aging, analogous to development, may be referred to as the collective of changes which occur during the entire life span of a biological system. Aging of function, organs and cells, is universal among all multicellular organisms. It has been determined that genes are involved and program a species to a maximum life span characteristic to that species. Proteins, combinations like glycoproteins or lipoproteins, structural proteins, enzymatic proteins and others are also relevant to the aging process. Environmental factors have also been shown to change even an inherited tendency for long life.

In the cross-linking theory of aging, increasing numbers of bonds are formed between critical molecules, wherein molecules such as enzymes, for example, are prevented from performing their cellular functions. Aging produces changes in the processes of cellular genetic information transfer. Age changes have also been found in chromatin structure, in the repair of DNA, in RNA synthesis, as well as in the structure of proteins. Peptide hormone trophic factors, like nerve growth factor (NGF), platelet derived growth factor (PDGF), interferon, interleukins, protons, electrons, trace metals are all important in relation to aging.

When considering the aging process, aging may be thought of as a slow burn of body parts. A type of biological fusion occurs which is similar to thermonuclear fusion, whereby nuclei are fused forming heavier nuclei and releasing energy. Such fusion is responsible for radiation burns, and produces increased scar tissue (granulation tissue). This energy produces heat which increases the agitation of the constituent parts of the biological system. This agitation increases scar tissue because the system must introduce a defensive structure to accommodate the intrusion of increased chaos within the statistical limits of the lattice structure so designated. Normal oxidation-reduction processes produce heat which increases tendency towards chaos, anisotrophy, and disruption of a practical level of being. Chromosomal damage, cross-linking in chromosomes, improper genetic information transfer and improper structures of encoded proteins will lead to an increase in scar tissue production.

Regeneration is essential to the reversal of aging products such as scar tissue. Good nutrition is also advisable to maximize the effects of a program which strives for the increase of life expectancy.

It has been noted that concentration of metal ions increase dramatically with age in cells. Sources of ions like calcium, magnesium, copper, zinc, sodium, potassium are food eaten and air breathed. Excess metal ions or metal ions improperly distributed in the cell will produce genetic information transfer errors.

In the past, a number of procedures have been described which involved the employment of magnetic fields to treat various diseases. Devices for applying electromagnetic energy to living tissue are disclosed, for example, in U.S. Pat. No. 2,099,511 to Caesar, U.S. Pat. No. 2,103,440 to Weissenberg, and U.S. Pat. No. 781,448 to McIntyre. Caesar teaches applying an alternating magnetic field to a localized area, and it is also believed to rely primarily on localized heating (diathermy). Weissenberg teaches application of a low level field and McIntyre teaches applying a homogeneous field to the whole body of a plant or animal, for therapeutic reasons. These patents demonstrate the interest in application of electromagnetic energy to plants and animals for therapeutic reasons, but do not teach any particular means for determining a field strength or frequency that will have any particular beneficial effects. Furthermore, these methods do not specifically address ameliorating the products of aging.

In connection with accelerating healing of traumatic injuries, U.S. Pat. Nos. 4,611,599 and 4,576,172 both to Bentall, and U.S. Pat. No. 3,890,953 to Kraus et al. and U.S. Pat. No. 3,738,369 to Adams et al., induce particular fields for promoting growth of damaged tissue. Bentall teaches RF frequencies and Kraus teaches power line frequencies.

Of course with the variations in power level from diathermy to the microwatt levels of the Bentall patent, and frequencies which vary over similar orders of magnitude, there is no reference that provides any rationale or means for calculating particular magnetic flux densities and alternating polarity field frequencies that will have any particular effect specific to defined elements of the plant or animal.

U.S. Pat. No. 5,269,746 to Jacobson, the inventor herein, describes a therapeutic treatment of mammals for disease by subjecting mammals suffering from certain diseases to an alternating magnetic field having flux density and a frequency calculated as a function of the mass of a specified target. The calculation is such to equate the energy of a current electromagnetically induced in the mammal with the gravitational energy for the target genetic material, such that a dual resonance is achieved. The Jacobson patent uses low level mass-characteristic fields and thus avoids disadvantages of prior art methods, characterized by high power, high frequency, and levels not related to target masses.

The Jacobson patent, however, specifically relates to "targets" relative to the diseases disclosed therein and specifically focuses on the disease etiology. The Jacobson patent does not address the "targets" which would be considered fundamental and basic to biological function, the essence of aging, nor does it focus on "multiple targets" necessary for treating the affects of aging. Furthermore, the necessary vibrational energies in the metal ions required to affect aging require flux densities not disclosed or taught by the Jacobson patent. In order to affect aging, it is necessary to target a wide range of critically important molecules, extending to levels lower than the $6 \times 10^{-10}$ gauss disclosed in the Jacobson patent.

SUMMARY OF THE INVENTION

In accordance with its broadest aspect the invention relates to a method and apparatus for ameliorating the aging process and the effects of aging and maintaining the integrity of health. The method includes subjecting biological systems to alternating and steady magnetic fields having flux densities ranging from $10^{-6}$ gauss to $10^{-20}$ gauss and preferable frequencies from almost direct current to 100 Hertz. This range will depend on the particular application and could increase to over $10^{14}$ Hz. Flux density and frequency are calculated as a function of the mass of quantum genetic targets and associated structures thereof. Examples include genes (particular DNA segments), homeoboxes, RNA, protein, enzymes, hormones, neurotransmitters, water molecules, trace metals like calcium, protons and electrons. The calculation is made with reference to the equation $mc^2=Bvlq$, where m=mass; c=speed of light; B=magnetic flux density; v=intertial velocity of the mass contained in l; l=length of the conductive body (e.g., human being, cell, or DNA segment); q=unity. The calculation is such to equate the intrinsic energy of a target mass with the electromagnetic interaction energy produced from the interaction of the biological system with the magnetic field. The waveform may be sinusoidal, rectilinear, or any suitable waveform as determined by one skilled in the art. The process begins by targeting the larger targets first and then diminishing the field magnitude slowly and incrementally according to the targets. The frequency when alternating current (AC) is indicated is calculated with the cyclotron resonance formula, $f_c=qB/2\pi m$. The apparatus includes a specially constructed pool for generating the specific magnetic flux necessary for treatment. Orientation of the patient with reference to the earth's position relative to the sun may be taken into account. Furthermore, the patient may be in an upright, prone or swimming position depending on the specific treatment scheme.

BRIEF DESCRIPTION OF THE DRAWINGS

Having briefly described the invention, the same will become better understood with the following detailed description, taken in conjunction with reference to the attached drawings in which.

DETAILED DISCUSSION OF THE INVENTION

The method of the present invention generally includes subjecting biological systems to alternating and steady magnetic fields having flux densities ranging from $10^{-6}$ gauss to $10^{-20}$ gauss and frequencies from almost direct current to $10^{14}$ Hertz, preferably below 100 Hz. Patients are subjected to various flux densities with various patient orientations with respect to the earth in relation to the sun, as will be illustrated in the following illustrative examples of treatment.

Flux density and frequency are calculated as a function of the mass of multiple targets and associated structures thereof. Examples include genes (particular DNA segments), homeoboxes, RNA, protein, enzymes, hormones, neurotransmitters, water molecules, trace metals like calcium, protons and electrons.

The calculation is made with reference to the Jacobson Resonance equation $mc^2=Bvlq$, where m=mass; c=speed of light; B=magnetic flux density; v=inertial velocity of the mass contained in l; l=length of the conductive body; q=unity. The waveform may be sinusoidal, rectilinear or another. The process generally begins by targeting the larger targets first and then diminishing the field magnitude slowly and incrementally according to the targets. The frequency when AC is indicated is calculated with the cyclotron resonance formula, $f_c=qB/(2\pi m)$.

The apparatus includes a specially constructed pool for generating the specific magnetic flux necessary for treatment. Furthermore, the patient may be in an upright, prone or swimming position depending on the specific treatment scheme.

Figure 1:
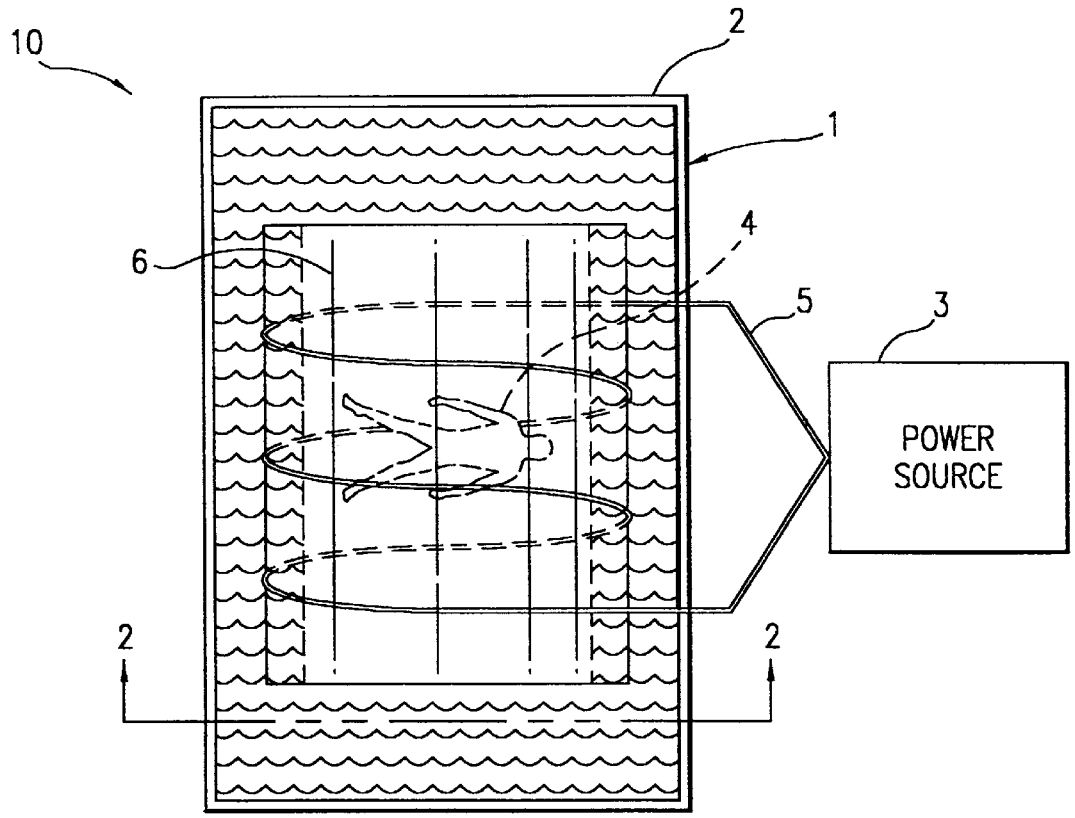
FIG. 1 shows a top view of an apparatus for providing the electromagnetic flux used in the treatment in accordance with the invention, showing the patient in a prone position.
Figure 2:
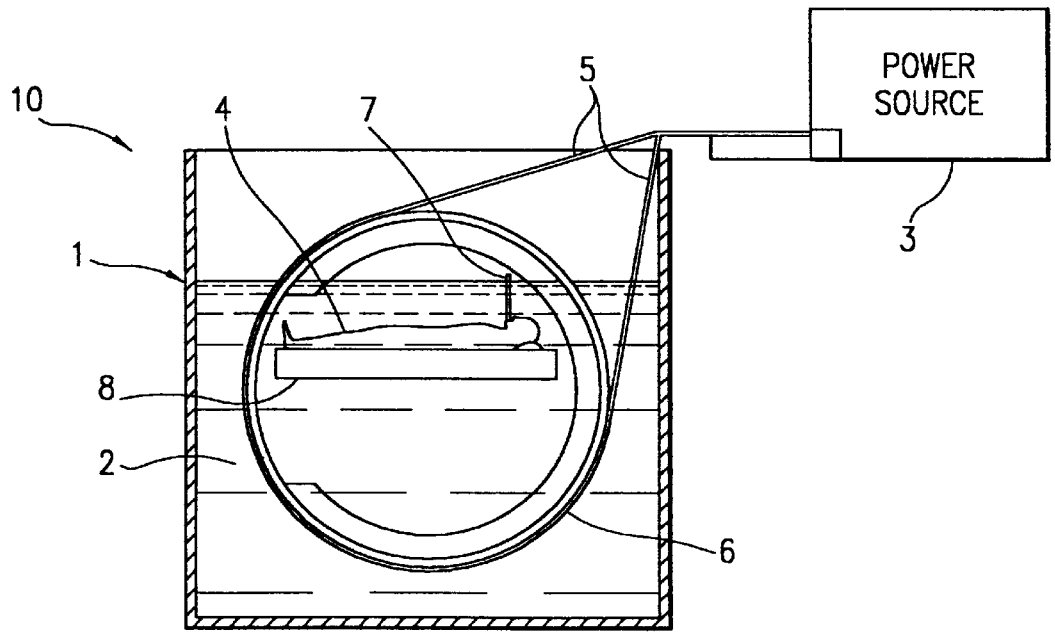
FIG. 2 shows a cross-section of FIG. 1 taken along line 2—2.

FIG. 1 shows a top view of an apparatus 10 for providing the electromagnetic flux used in the treatment in accordance with the invention, showing the patient 4 in a prone position. FIG. 2 shows a cross-section thereof taken along line 2—2. Means for subjecting a patient to specific magnetic fields may include in part a water medium 2 within which the patient 4 is immersed, and which, is held in a tank 1 of sufficient size to hold a solenoid 6, which itself forms a part of means for generating one of a plurality of electromagnetic fields. A breathing apparatus, such as a snorkel 7 is provided. A flotation device 8 is also provided. The solenoid 6 is comprised of a column created by the continuous turns of the electrical conductive wire 5, the respective ends of which are connected to an electrical power source 3 also forming a part of the means for generating one of a plurality of electromagnetic fields, as further described with reference to the specific fields in the description of the apparatus 10 and its specific structure set forth in Examples 1–4. When the power is turned on, an electromagnet is created which generates the magnetic field to which the patient 4 is exposed and which is used in the practice of the instant invention.

Figure 3:
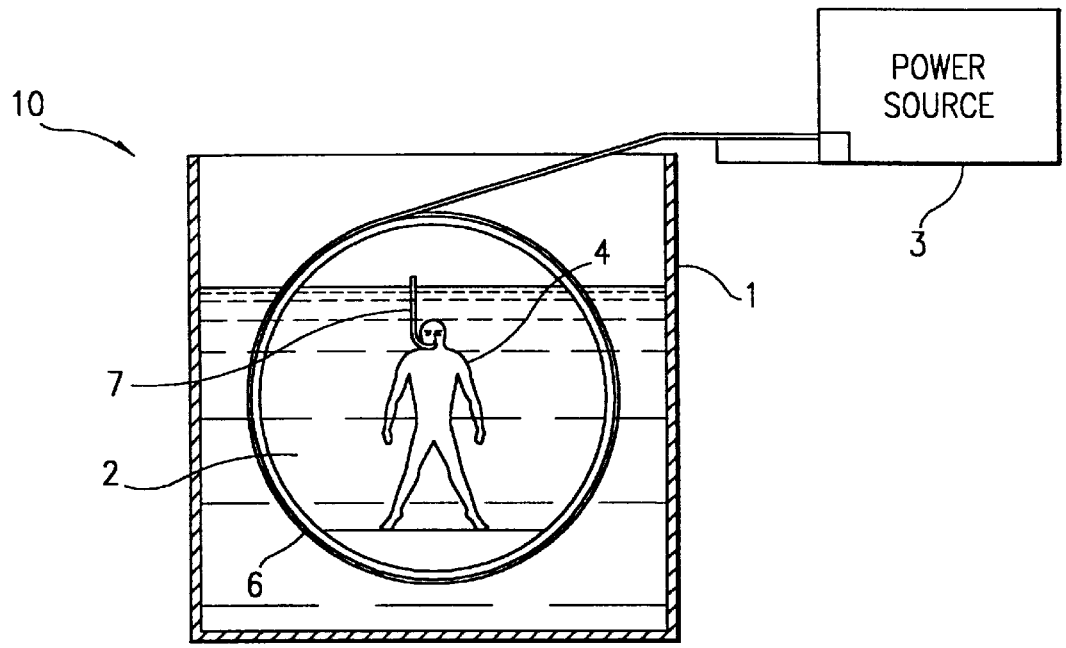
FIG. 3 shows a cross-section of an alternate orientation of the patient in the apparatus of FIG. 1, showing the patient standing in the water.

FIG. 3 shows an alternate orientation of the patient 4, namely standing in the water 2. Again, water medium 2 within which the patient 4 is standing is held in a tank of sufficient size to hold the solenoid 6. Breathing apparatus, such as a snorkel 7 is provided such that the patient 4 is completely immersed. A power source 3 is provided.

Figure 4:
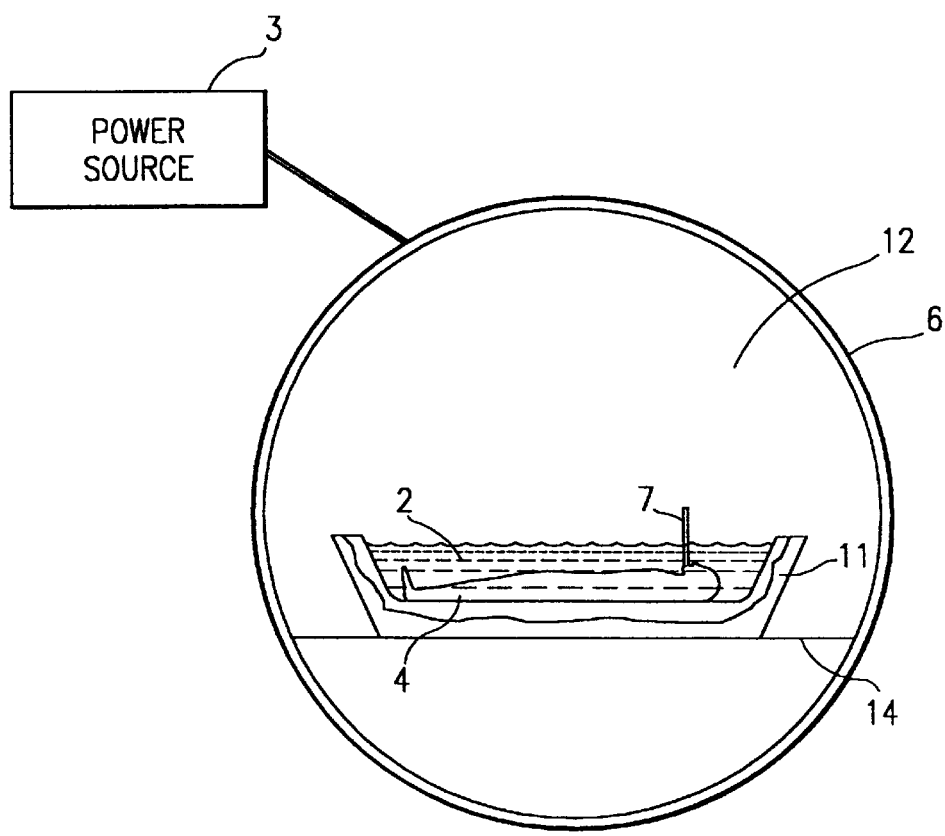
FIG. 4 shows a cross-sectional view of a solenoid surrounding a bathtub of water, with air in the area therebetween in accordance with an alternate embodiment.

Alternately, the solenoid may surround a bathtub 11 of water 2, with air 12 in the area therebetween, as shown in FIG. 4. The patient 4 may be treated in a prone position, utilizing a snorkel 7 or other breathing apparatus. The bathtub 11 may be filled with water 2. The bathtub 11 could rest on a surface 14.

Figure 5:
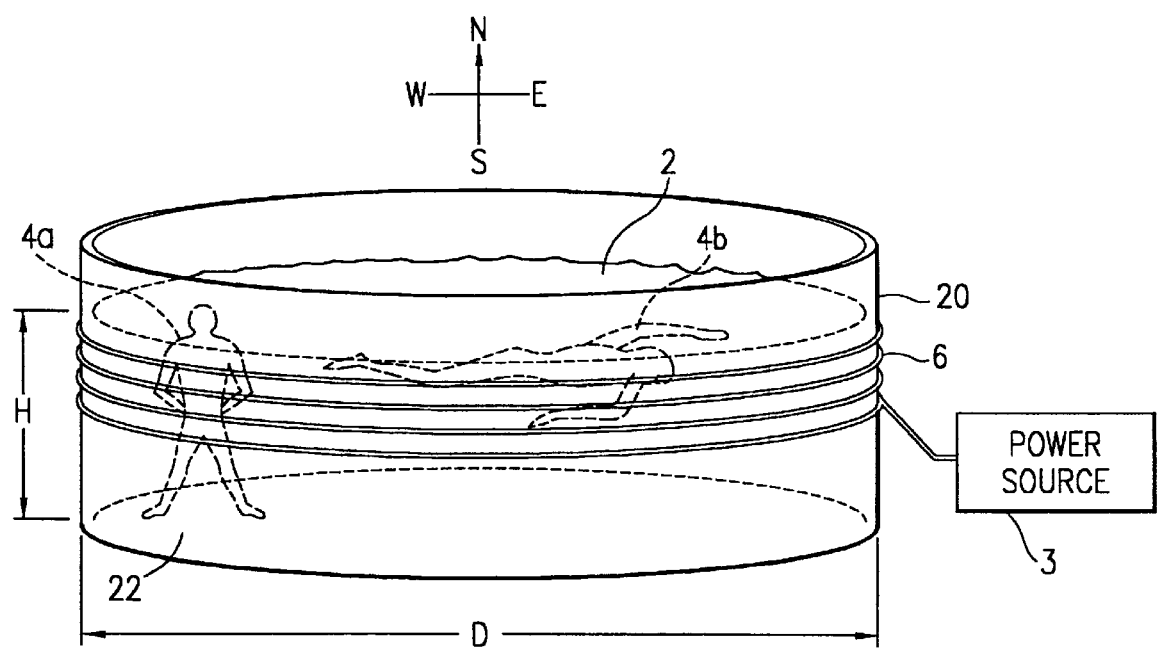
FIG. 5 shows a pool in an alternate embodiment, in which the patient may stand or swim.

Turning now to FIG. 5, a pool 20 filled with water 2 is provided, in which the patient may stand 4a or swim 4b. The water depth (H) is variable, but preferably at least 6 feet deep. A non-magnetic floor 22 is provided. The solenoid 6 surrounds the pool 20 and has a power source 3 connected thereto. The pool 20 itself would also be non-magnetic. It is believed this would be the most pragmatic embodiment of the invention, although optimally the pool should be placed in the midst of a very large solenoid. (See Example 4). The directions, North, South, East and West are marked in the drawing for patient orientation. The diameter (D) of the pool 20 would be sufficient to allow the patient to swim 4b.

The following illustrates utilization of the pool setting. First, when v=orbital earth velocity, when the patient walks North/South upright, there is maximal interaction with the geomagnetic and some interaction with flux lines produced by the pool solenoid. When v=orbital earth velocity, the middle of the afternoon or the middle of the night are the best times for treatment.

When the patient swims (horizontally) North/South, there is maximal interaction with weak solenoidal field and some interaction with the geomagnetic. Treatment times would include sun up and sunrise when v=earth velocity.

When the patient swims (horizontally) East/West (see 4b in FIG. 5), he maximizes both interactions of geomagnetic and solenoidal. Treatment times are sun up and sunrise when v=orbital velocity of the earth.

When the patient walks upright East/West (see 4a in FIG. 5), he maximizes the geomagnetic interaction and has some interaction with the solenoidal field. Treatment times include middle afternoon, middle of the night when v=orbital velocity of the earth.

In the pool setting of FIG. 5, the following treatments include when v=rotational earth velocity. (1) Orientation= vertical North/South movement. Time=anytime of day. Results=maximum geomagnetic and some solenoidal. (2) Orientation=horizontal North/South movement. Time= anytime. Results=some geomagnetic and maximum solenoidal. (3) Orientation=horizontal East/West movement. Time= anytime. Results=some solenoidal and some geomagnetic when v=rotational diminished effect due to movement of the conductor through space. (4) Orientation=vertical East/West movement. Time=anytime. Results=maximum geomagnetic and some solenoidal. The above shows the need to vary the movements in the pool throughout exposure time.

Fields will range from about $10^{-6}$ G to $10^{-20}$ G and will be changed incrementally, according to relevant targets, e.g., genes. These effects are integrated overtime and it may be necessary to expose the patient for 20 minute periods every day for three weeks to observe changes in function and structure.

The structural changes may be subtle, and represent reorientations of spin angular momenta of leptons and baryons which adjust the spatial orientations of molecules with respect to one another, the defining element of life. It is believed that this treatment will reduce the loss of elasticity on skin, tendons and blood vessels that occur with age. The increase in cross-links contributes to the loss of elasticity. The treatment may decrease the number of cross-links by improving the function of the whole organism by restructuring. Furthermore, multiple harmonic interactions of physiologic magnetic fields may be controlled.

Homeotic genes, those which determine what body parts become, are key targets for purposes of tissue regeneration. Homeoboxes are those DNA segments which are considered most important for the function of the genes. NIR's have been demonstrated to regulate cell motility, growth, plarity and DNA transcription. Control over what effects NIR's produce may only be derived through an understanding of the fundamental physico-mathematical mechanism of interaction between biological systems and EMFs. The internal structures, distributions and densities of trace metals, which have been shown to be connected to errors in information transfer by genes may be controlled. Direct current (DC) fields can vibrate particles from $10^{11}$ Hz to $10^{14}$ Hz including genes and proteins. Alternating current (AC) fields may be calculated using ion cyclotron resonance in conjunction with Jacobson Resonance. $10^{-20}$ G fields may be used to vibrate neutrinos, another subtle critically important target. Exposure time is preferably minimally three weeks, twenty minutes per day, everyday exposure or continuous at the lowest levels from $10^{-8}$ G and weaker.

EXAMPLE 1

A solenoid comprised of forty turns of germanium wire (55 ohms/cm) is prepared. The interior core of the solenoid has a radius of 1.5 meters, and the length is about 6.15 meters. The solenoid is placed in a waterproof bathtub (e.g., pool) 18 meters in length, 9 meters in width, and 9 meters in depth, so as to manufacture clearance for magnetic flux, and immersed in water (ordinary sea water), to a level reaching two-thirds of the diameter of the inner core of the solenoid. A styrofoam body holder, into which the human is placed in a prone position, is oriented so that the body's long axis thereof is in an east-west orientation while magnetic lines of flux are oriented in a north-south angulation. The times of exposure are sunrise and sunset so that the direction of (v) earth's movement through space as it orbits the sun, is at an approximate right angle to the longitudinal axis of the human biological system. A potentiometer regulates the electrical current which flows through the germanium wire comprising the cords of the solenoid.

Treatment comprises the following seven steps:

(1) A magnetic field is created in the water about the human system which is about $6.67 \times 10^{-6}$ gauss. The biological system (human) is held therein subject to a flux density of $6.67 \times 10^{-6}$ gauss for two minutes. The wave form of the signal is biphasic and rectilinear while the frequency is 0.1 Hz. The current (I) is about $10^{-5}$ amperes.

(2) The current is adjusted to $10^{-6}$ amps and the magnetic flux density (B) to $6.67 \times 10^{-7}$ gauss. The frequency is 0.01 Hz. This signal is maintained for two minutes.

(3) Following the above exposure the current (I) is changed to about $10^{-7}$ amps, the flux density (B) to $6.67 \times 10^{-8}$ gauss, and frequency ($f_c$) to 2.1 Hz. This signal is maintained for five minutes.

(4) Then the signal is changed to $10^{-8}$ amps in the coil, (B) is $6.67 \times 10^{-9}$ gauss, and $f_c$ is 0.21 Hz. This signal is maintained for two minutes.

(5) Then the signal is changed to $10^{-9}$ amps, $6.67 \times 10^{-10}$ gauss, and $f_c$=0.02 Hz, for a period of two minutes.

(6) Then the signal is changed to $6.67 \times 10^{-11}$ gauss, the current to $10^{-10}$ amps, and $f_c$ is 0.002 Hz, to be maintained for two minutes.

(7) Finally, the current is changed to $10^{-11}$ amps, (B) to $6.67 \times 10^{-12}$ gauss, and $f_c$ to 0.0002 Hz, for three minutes.

The total treatment time is eighteen minutes. The waveform remains rectilinear and biphasic throughout the exposure. This treatment will be repeated three times a week for three weeks after which time noticeable improvement will be manifested.

It is believed this treatment scheme will provide the following results. Internal changes, seen on a cellular level include fewer errors produced by genes in protein synthesis that enable cells to fulfill their basic functions. Fewer mutations of somatic cells will occur slowing deteriorative changes. Fewer cross-links are formed, such that fewer numbers of bonds are formed between important molecules such as enzymes enabling improvement of cellular functions. Immunological function will improve such that the body's protective reaction against foreign proteins or disease-causing organisms will improve. Autoimmune function will improve, as the number of autoimmune antibodies in the blood will decrease. Incidence of "immune diseases" will diminish. Functional ability of the heart is improved and death of heart muscle cells is greatly diminished. Arteries become more flexible, and maintain their shapes, and blood pressure will be improved and stabilized. Atherosclerosis (characterized by deposition of cholesterol in the arteries), hypertension, and arteriosclerosis all will diminish. Chance of stroke will diminish. Amyloidosis decreases.

External, visibly notable improvements may include improvement in elasticity in skin, (in addition to tendons and blood vessels). It is also believed that cardiovascular function improves as do vital signs. Hair loss may diminish in addition to the slow down of graying of hair. Deteriorative change in skin, hair, and skeletal and muscular systems may slow. Hair growth may speed up, skin may become smoother, and spots of deepened pigment may be diminished. There may be improvement in posture, and movement becomes easier and quicker. Memory may improve, and over-all cognitive function may improve. Sexual capacity may improve. Prostate problems in men may decline. Taste, smell, touch and sensitivity to vibration may improve. Arthritis may be diminished. Sense of time, place, and performance of intellectual tasks may improve. Emotional problems may diminish.

In the aged, it is further believed that cerebral arteriosclerosis and senile brain diseases will be ameliorated. Glaucoma is ameliorated as well as muscular degeneration slowed. Bone and joint disorders improve. Increase in kinesthesia results (the sensations of bodily position and movement received from muscles and joints). Osteoporosis decreases (the loss of density of bone occurring most frequently in postmenopausal women). Osteoarthritis, or degenerative joint disease is diminished. Oncogenic transformations diminish. An increased ability to handle glucose also results, i.e., diabetes in ameliorated. Chronic obstructive pulmonary disease is diminished.

EXAMPLE 2

A solenoid comprised of a hundred turns of copper wire (gage 37), 533.4 ohms/1,000 ft. at 25° C. is prepared. The body of the cylindrical core is a non-magnetic substance, having a diameter of 8 ft., and is 12 ft. long. A water proof, non-magnetic bathtub is placed into the solenoid and ordinary ocean water is placed into the bathtub. The solenoid is placed in an environment which has minimal magnetic noise, i.e., far from power lines, air conditioning vents, magnetic objects having a high relative permeability such as iron. A super conducting quantum interference device (SQUID) is utilized to measure the intensity of the magnetic fields, both outside the solenoidal system and inside, to ensure lack of interference of magnetic noise as well as to determine the magnetic flux density of the created signal in water, with a preferable homogeneous isotropic signals inside the solenoidal system. The long axis of the solenoid is placed in a north-south orientation to minimize interference with the geomagnetic field. The human to be treated is placed in an east-west orientation during treatment, sunrise and sunset, while in a prone position. During midnight and midday the patient may stand. Mu metal, a metal which blocks magnetic noise, as well known in the art, may be used on the walls of the treatment room to block out noise but the geomagnetic field will still come up from the floor.

The treatment comprises a six day regime. On the first day, the human subject will be subjected to a magnetic flux density of $7 \times 10^{-8}$ gauss, at a frequency of 2.1 Hz, to begin treatment while employing a rectilinear waveform. This treatment will last twelve minutes. The second day the subject will be exposed to a nanogauss flux density (B), at a frequency of 0.03 Hz, employing a rectilinear waveform for a period of twelve minutes. The third day the exposure is $10^{-10}$ gauss (B), $f_c=0.0003$ Hz, and rectilinear waveform for fifteen minutes. The fourth day the exposure is $10^{-11}$ gauss, $f_c=0.0003$ Hz, and rectilinear waveform for twenty minutes. The fifth day the exposure is $10^{-12}$ gauss, first at 0.01 Hz for ten minutes, then at 0.00003 Hz for twenty minutes, and rectilinear waveform. The sixth day the exposure is at $10^{-16}$ gauss at $f_c=3 \times 10^{-9}$ Hz for thirty minutes using a rectilinear waveform.

This treatment may be done in air, although water is preferable. The treatment should be repeated for three weeks and then patient examination is carried out. There is no limit as to how often this treatment may be accomplished, although periodic evaluation of subject's responses should be done every two months. The subject may select to be treated in either air or water at any point during the process to maximize comfort.

EXAMPLE 3

A solenoid comprising germanium wire (55 ohms/cm) or copper wire, using forty turns, is prepared in the form of a circular pool six feet deep. Water level (sea water or salted distilled water), is adjustable to accommodate the height of the human subjects. During sunrise and sunset, subjects are horizontal (swimming); and the middle of the night and midday of the afternoon, subjects are standing or walking upright.

The treatment schedule includes the following flux levels, frequencies, preferably with a rectilinear waveform, and time periods indicated.

1. (B)=$3 \times 10^{-7}$ G; ($f_c$)=9 Hz; (one minute).
2. (B)=$7 \times 10^{-8}$ G; ($f_c$)=2.1 Hz; (2 minutes).
3. (B)=$5 \times 10^{-8}$ G; ($f_c$)=1.5 Hz; (1 minute).
4. (B)=$3.4 \times 10^{-8}$ G; ($f_c$)=1.02 Hz; (1 minute).
5. (B)=$5 \times 10^{-9}$ G; ($f_c$)=0.15 Hz; (2 minutes).
6. (B)=$1 \times 10^{-9}$ G; ($f_c$)=0.03 Hz; (2 minutes).
7. (B)=$7 \times 10^{-10}$ G; ($f_c$)=0.021 Hz; (2 minutes).
8. (B)=$6 \times 10^{-11}$ G; ($f_c$)=0.002 Hz; (2 minutes).
9. (B)=$3 \times 10^{-12}$ G; ($f_c$)=$10^{-4}$ Hz; (2 minutes).
10. (B)=$1 \times 10^{-12}$ G; ($f_c$)=0.01 Hz (1 minute and ($f_c$)=$3 \times 10^{-5}$ Hz (1 minute).

11. (B)=$10^{-14}$ G; ($f_c$) $3\times10^{-7}$ Hz; (1 minute).
12. (B)=$10^{-16}$ G; ($f_c$) $10^{-8}$ Hz; (1 minute).
13. (B)=$10^{-20}$ G; ($f_c$) $10^{-12}$ Hz; (1 minute).

Treatment is twenty minutes in the pool. Treatment should be done three to four times a week for one month before evaluation of effects. Routine exposure to these complex of signals is indicated for maintenance of well being.

The subjects in this example may swim or walk upright at any time of day or night if the coils are wrapped around the pool. Variation of exposure positions will work. North-South orientation of flux lines is always preferred to minimize interference with the geomagnetic. Relatively vertical orientation of flux lines in a pool setting require subjects to be swimming at least part of the time because the magnetic flux, the long axis of the body and (v) of the earth directions should be orthogonal.

Figure 6:
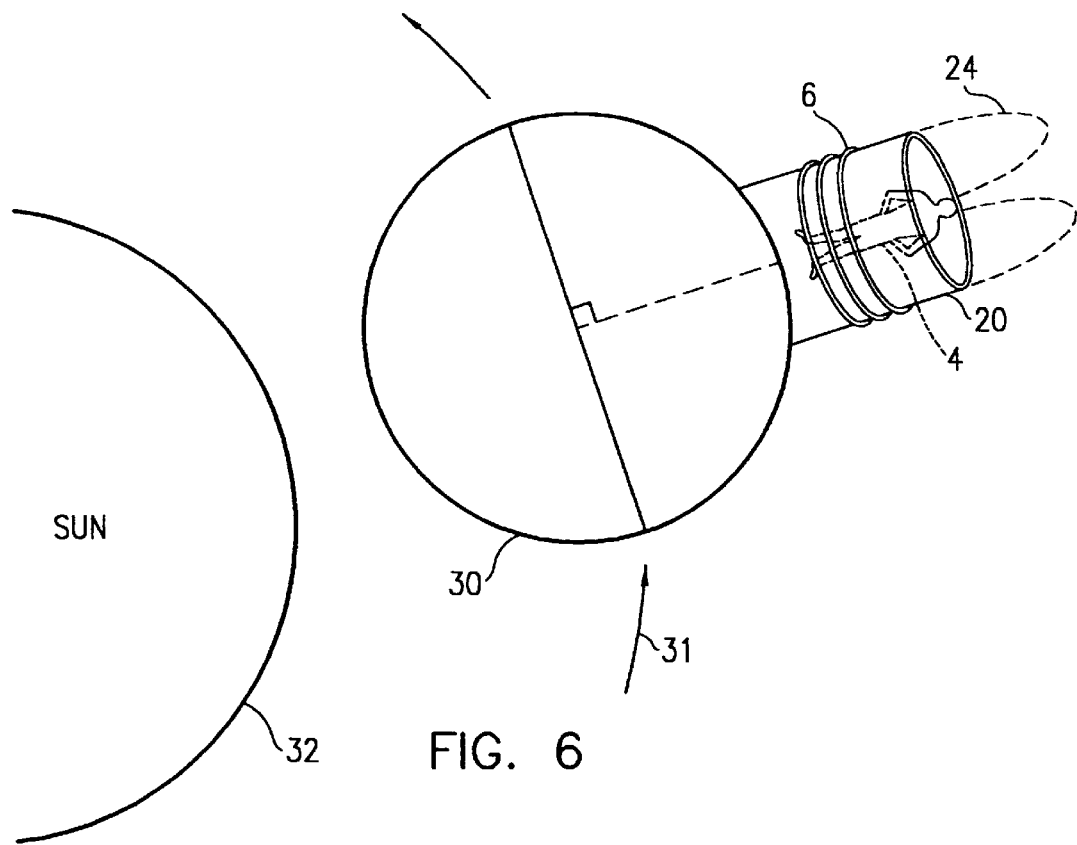
FIG. 6 illustrates a variation of exposure positioning in relation to the orbital direction of the earth and patient orientation, wherein the patient is standing in the pool, parallel to flux lines.

FIG. 6 illustrates one variation of exposure positioning, although not optimal. The coils of the solenoid 6 are wrapped around the circular pool 20. The direction 31 of the earth 30 about the sun 32 is approximately perpendicular to the flux lines 24. The long axis of the subject 4 is parallel to the flux lines 24. This is not considered optimal, but if the subject moves into different positions, there will be a positive effect. East-West is satisfactory but not optimal.

Figure 7:
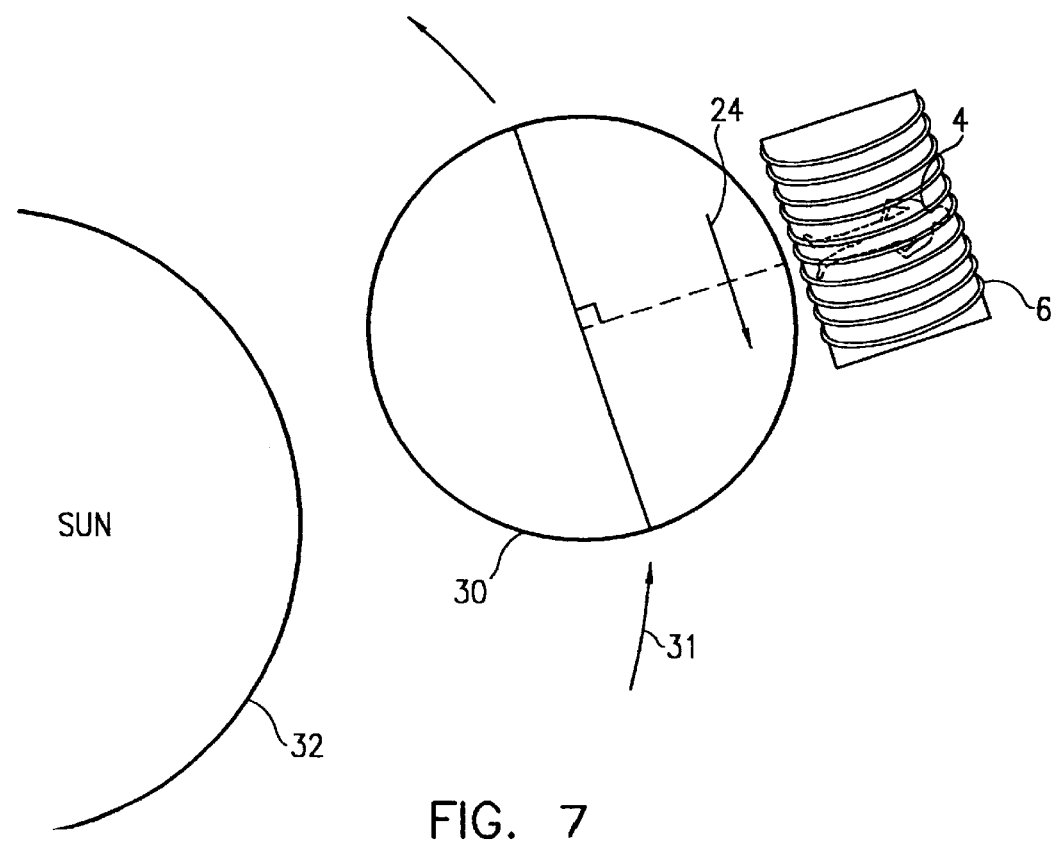
FIG. 7 illustrates another variation of exposure positioning in relation to the orbital direction of the earth and patient orientation, wherein the patient is East-West or standing perpendicular to the flux lines in the solenoid and perpendicular to the direction (v) of the earth.

FIG. 7 illustrates another variation of exposure positioning. The subject 4 is East-West or standing perpendicular to the flux lines 24 in the solenoid 6 and perpendicular to the direction 31 (v) of the earth 30 about the sun 32. This is midday or midnight positioning and is considered good positioning.

Figure 8:
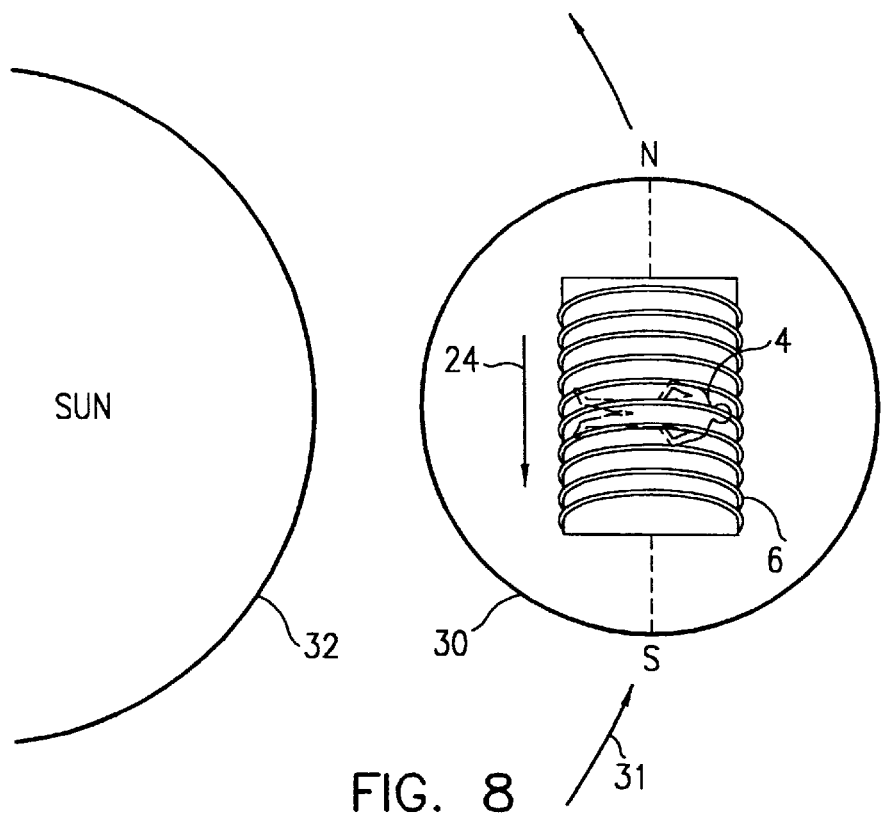
FIG. 8 illustrates another variation of exposure positioning in relation to the orbital direction of the earth and patient orientation, wherein the patient is oriented East-West and perpendicular to the flux lines of the solenoid and geomagnetic field.

FIG. 8 illustrates another variation of exposure positioning at sunset or sunrise. The patient 4 is oriented East-West. The patient is perpendicular to the flux lines 24 of the solenoid 6 and geomagnetic field. The patient's long axis and solenoid's flux lines are relatively perpendicular to (v) direction 31 of the earth 30 as it moves in orbit about the sun 32.

Figure 9:
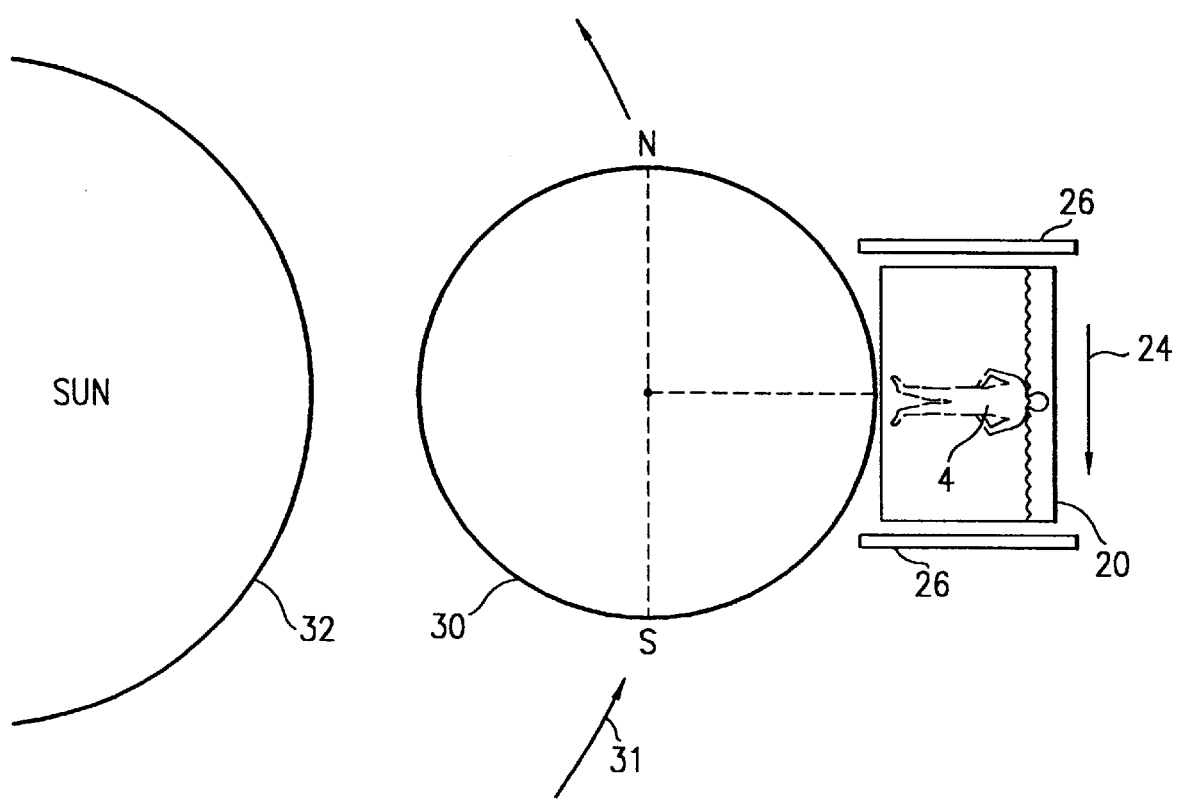
FIG. 9 illustrates another variation of exposure positioning in relation to the orbital direction of the earth and patient orientation, wherein the direction of flux is North-South and the patient is standing in the pool perpendicular to the flux lines and the direction of the earth.

FIG. 9 illustrates another variation of exposure positioning where the direction of flux 24 is North-South and the patient 4 is standing at midday or midnight to be perpendicular to the flux lines 24 and the direction 31 of the earth 30 about the sun 32. The patient is within the pool 20, which is between two plates or poloidal magnets 26.

Figure 10:
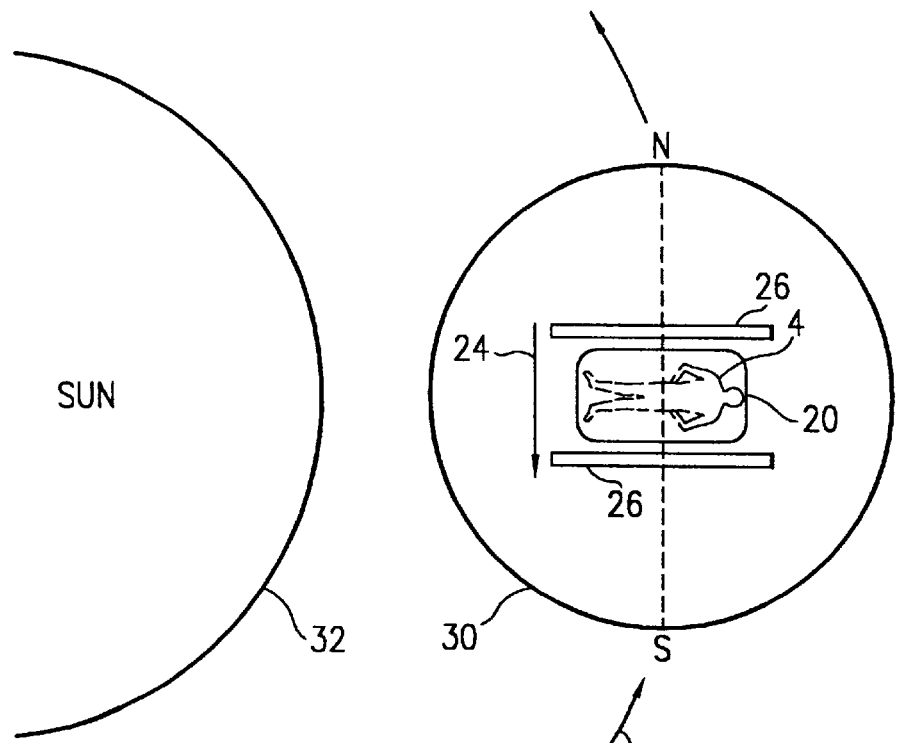
FIG. 10 illustrates another variation of exposure positioning in relation to the orbital direction of the earth and patient orientation, wherein the long axis of the patient is perpendicular to the direction of the earth and to the flux lines and geomagnetic, and the patient is in East-West swimming orientation within the pool.

FIG. 10 illustrates another variation of exposure positioning where the long axis of the patient 4 is perpendicular to (v) the direction 31 of the earth 30 and to the flux lines 24 and geomagnetic. The patient 4 is in East-West swimming orientation within the pool 20 at sunrise or sunset. Two plates or poloidal magnets 26 are located on either side of the pool 20.

EXAMPLE 4

Figure 11:
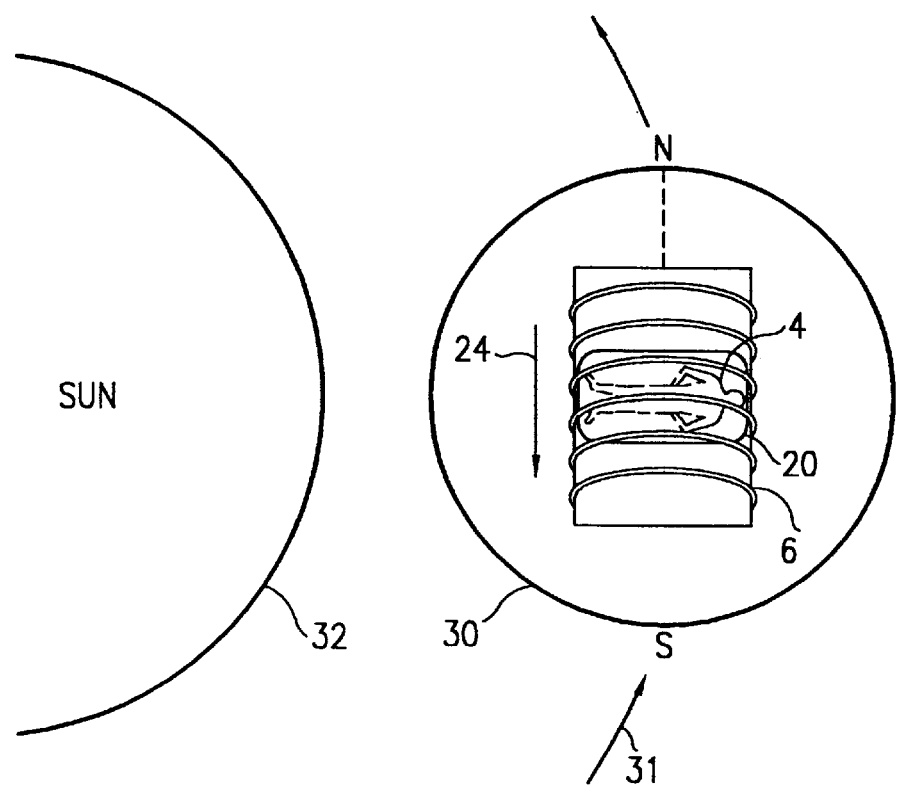
FIG. 11 shows the patient orientation and specific apparatus is illustrated wherein the setting is a pool within a large solenoid and the patient is swimming East-West.

Turning now to FIG. 11, the patient orientation and specific apparatus is illustrated. A potentiometer is power source. The setting is a pool 20. Flux lines 24 are created by the means for generating one of a plurality of magnetic fields, in this case, plates, poloidal magnets (rings), Helmholz coils (rings in series) or a optimally very large solenoid 6 with a round swimming pool 20 in the middle. (As in FIGS. 4 or 5). The pool 20 is preferably 15 feet in diameter (D), 6 feet deep. Copper wire (gage 22) may be used for the solenoid 6 which is twenty feet in diameter and twenty-five feet long. The water level is preferably 4 feet. The pool 20 may be suspended with non-magnetic materials within the solenoid 6. The time for treatment would be sunrise or sunset. The apparatus would resemble FIG. 10, except for a large solenoid. Patient 4 is in East-West swimming orientation.

The six-day treatment schedule, in representative flux densities, frequency and time, follows:

(1) B=$7\times10^{-8}$ G; $f_c$=2.1 Hz; time=12 minutes;
(2) B=$1\times10^{-9}$ G; $f_c$=0.03 Hz; time=12 minutes;
(3) B=$3\times10^{-10}$ G; $f_c$=0.009 Hz; time=15 minutes;
(4) B=$6\times10^{-11}$ G; $f_c$=0.002 Hz; time=20 minutes;
(5) B=$1\times10^{-12}$ G; $f_c$=$10^{-4}$ Hz; time=25 minutes;
(6) B=$1\times10^{-16}$ G; $f_c$=$10^{-8}$ Hz; time=25 minutes;

No treatment is given on the seventh day. The schedule is repeated for four weeks. Then the patient is evaluated.

Jacobson Resonance induces ordering interactions with external magnetic fields, using biomagnetic fields ($10^{-5}$ G to $10^{-20}$ G) on oncogene genetic material.

Oncogenes code altered growth factors and appear to be structurally very close to normal genes. These appear to be like the rest of the DNA structure, as piezoelectric crystalline structures that can be defined physically as an aggregate of atoms of whose integrated vector has a quantum magnetic moment that can be influenced by external electromagnetic (EM) fields.

It is believed that this interaction is an opportunity to reorient altered submolecular magnetic domains by placing the patient in a large water tank and exposing him to a 'virtually' static magnetic field (frequency of $10^{-6}$ Hz) with an intensity equal to physiological biomagnetic fields of $10^{-8}$ G. If the amplitude of the field is adequately modulated there would be quantum genetic resonance phenomena, the transformation of oncogenes into normal genes could follow. This may lead to therapeutic applications in terminal cancer patients and in patients suffering from other diseases, such as AIDS, genetic disorders and CNS regeneration, part of controlling the aging process.

The very weak intensity of the magnetic fields suggested revives the role of natural magnetic field, from the geomagnetic fields to spontaneous biomagnetism and of correlated physical phenomena such as the extremely weak magnetic resonance at geomagnetic field values.

This is consistent with cyclotron resonance of ions in the transmembrane channels exposed to a weak extremely low frequency (ELF) field, such as less than 150 Hz., and at the same time to the ever present earth magnetic (0.5 G).

Windows are considered, not just of magnitude and frequency of changing field but of exposure time due to the great variety of resonant interactions at different frequencies.

Senescent effects cannot be measured in cell culture due to problems of sterility after 100 generation. With a calcium ion for the target mass, $Ca^{++}$ q/($2\pi r$) of 760 C/g and a field flux density of $10^{-9}$ G or $7.6\times10^{-7}$ Hz therapeutic signals, biological amplification is dependent upon chronobiological processes that clearly produce windowing the first stage of which can be seen in cell structures, showing changes in transcription and translation. After twenty minutes, cellular effects from ELF electromagnetic fields (EMFs) may be maximum and then decline again, to rise again at an exposure window; e.g., three hours later, or two weeks later.

Smoothing the field, diminishing the field from maximum to minimum therapeutic signal, very slowly, will remove biologically disordered impurities from biological matter including viruses. Biological matter is in a state which may be designated a novel quantum liquid propitiatory of fractional solitons, fractions of the flux quantum $e^2/h$ with respect to the fractional quantum Hall effect. Vibrating masses will increase heat, and then gradually slowly cool as vibrations are diminished. Crystals will form for elimination by the body.

In discussing the derivation of Jacobson Resonance is it noted that Einstein's formula, $E=mc^2$, points to the gravitational potential of a mass, (m) is an inertial mass and ($mc^2$) refers to the intrinsic energy of the mass inclusive of the gravitational aether. Induced electromotive force $|\bar{\xi}|$ is equal to Bvl. The symbol $|\bar{\xi}|$ means the magnitude of the average induced emf. Ideally, (l) is a straight conductor and Bv and l are mutually perpendicular. (B) is magnetic flux density, (v) is the inertial velocity (incessant cosmic motion) of the mass contained in (l), the length of the conductive body; e.g., the human being, cell, or DNA segment. Generalizing $|\bar{\xi}|=(\bar{v}\times \bar{B})l$ or (v B sin θ)l, when l represents the distance the gravitational wave travels in a curved body. This will relate to geodetic, uniform translational systems to be considered in cases of DNA supercoiling, for example. Curling a body, while maintaining B, reduces strain by decreasing the energy of scalar deformation or vibrational energy. Indeed, smaller masses are consequently vibrated by coiling.

Because induced electromotive force $|\bar{\xi}|$ is equal to energy per unit charge by definition, energy (E) equals Bvlq. (q) is normalized and equal to unity as the voltage is electrical pressure and the gravity wave is a Lorentz force or elastic deformation, a push or pressure of the gravitational aether. The relationship Bvlq may be referred to as an electromagnetic interaction energy, or an energy of deformation of the scalar potential.

Thus, the Jacobson Resonance formula, $mc^2=Bvlq$ is a general form of resonance, related to both cyclotron resonance and Zeeman resonance. When (v) is the inertial velocity of the mass contained in the extended body (l) such as the orbital and rotational earth velocities and (c) is the speed of light, (l) refers to the length of the human or biological system and (m) refers to the quantum genetic character or associated structure thereof.

The diagrams of FIGS. 12a–d are proposed to explain Jacobson Resonance, $mc^2=Bvlq$, the equivalence of mass and energy with the joining of Einstein and Faraday. The casual nexus of natural phenomena involves the communication of motion through tough. A series of particle interactions are envisioned which produce an elastic deformation of aether albeit not directly perceivable. The aether has a motion of its own and does not participate in the creation of elementary electric charges. Yet there is a mechanical electromagnetic photon/phonon transduction or conversion that links EM field and the aether. Dark solitons, solitary wave solutions to non-linear problems, are examples of this virtual photon flux.

FIGS. 12a–d show the transfer of force from (q) charge. Weak magnetic fields, extrinsically sourced, produce a force acting on charged particles. Transfer of force to gravity waves are represented as well as the return of force to produce phonons in the EM field.

Figure 12A:
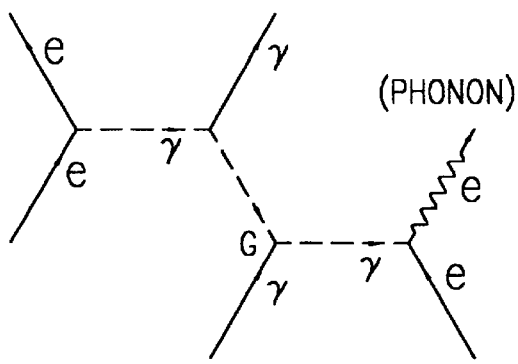
FIGS. 12a–d are mathematical vector diagrams showing the transfer of force from (q) charge.

In FIG. 12a, e→γ→G→γ→e. Force moves from the electron to the photon, carrier of light and electromagnetic radiation, then to a graviton carrier of elastic deformation of aether, back to a photon, and then finally the force is transferred to an electron.

Figure 12B:
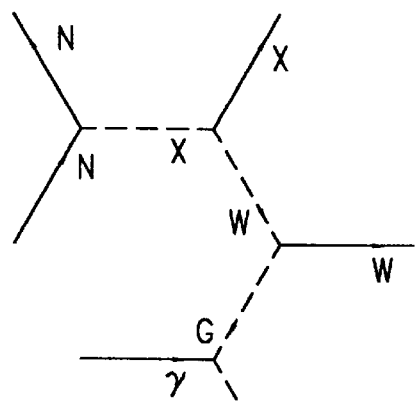

In FIG. 12b, N→X→W→G→γ→e. N=nucleon; X=carrier of strong force; W=weak boson; G=graviton; γ=photon; e=electron.

Figure 12C:
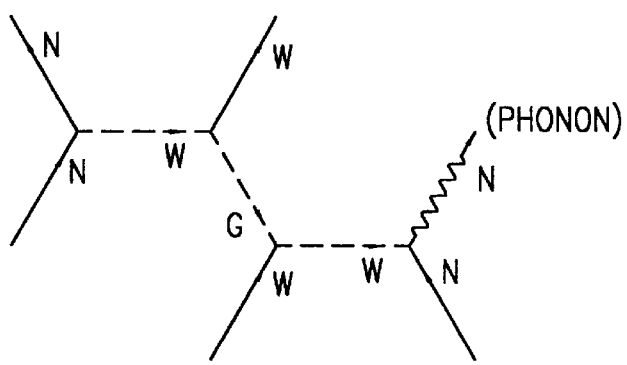

In FIG. 12c, N→W→G→W→N. Force moves from a nucleon to a weak boson, carrier of the weak force to a graviton, carrier of the gravitational force, back to a weak force carrier and then back to the nucleon.

Figure 12D:
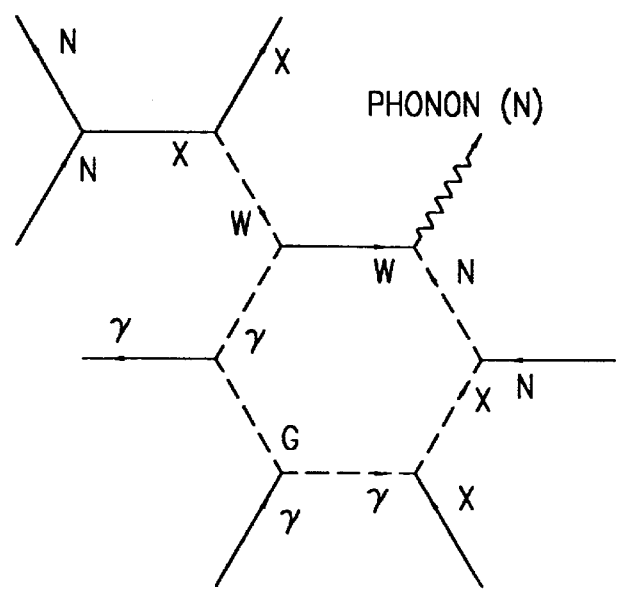

In FIG. 12d, N→X→W→γ→G→γ→X→N. N=nucleon; X=gluon (strong force carrier); W=weak boson (weak force carrier); γ=photon (quantum of light); G=graviton (constituent of gravitational aether); e=electron.

"Targets" are molecular weights of transforming DNA segments, viruses, and viral particulate matter enzymes, homeoboxes, peptide hormone trophic factors, hormones, neurotransmitters and antibodies. Energies of scalar deformation relate to solitary wave solutions for non-linear problems, as regions having different ground state configurations are separated by localized interfaces of infinite energy. Solitons have fractional, non-integral quantum or fermion numbers as ±⅓ and ±⅔. This vision also connects to the fractional and integral quantum Hall effects. Certainly, genes, proteins (α-halices or β sheaths, collagen) keratin, bone, cytoskeletal structures and centriloles are piezoelectric structures, converting EM oscillations to mechanical vibrations and vice versa.

Additionally, the (m) in Jacobson Resonance and charge (q) are not related. (q) is a universal, fundamental harmonic of charge. (m) and (l) travel with the earth, hurtling through space at 20 miles per second (as the earth orbits the sun) or at the rotational earth velocity (1,000 miles per hour). The force carrier of the magnetic field travels at the velocity of light (c), independent of its inertial or earth velocity. Therefore, the magnetic field is not said to be traveling with the earth as the human body is, according to the Special Theory of Relativity.

In Jacobson Resonance, (q) is a constant of proportionality in the same manner as (k) is in the Newtonian expression: (mdv)/dt=ma=kF. In Jacobson Resonance, electromotive force is defined as energy per unit charge. Therefore, (k) is equal to a single coulomb, and as voltage is electrical pressure, a gravity wave is energy of scalar deformation per unit charge.

Therefore, a system of dual resonance is established wherein (q) does not enter into the calculations. The elastic deformation of gravitational aether is a force which travels length (l) producing the harmonic energy.

In order to ascertain the potential hazard from an electromagnetic field, the following calculations are examined. Given a human biological system, there are a number of interactions which occur on cellular levels as well as organismic levels. When we take the target mass, for example to be $4\times10^{-22}$ grams (g) (approximately the mass of melatonin, physiologically active amines and even nucleotides) and multiply it by $c^2$ ($9\times10^{20}$ cm$^2$/sec$^2$, i.e., speed of light squared), then divide by human length, (l) $1.7\times10^2$ cm, this equals the force of the gravity wave. The gravity wave equals approximately $2\times10^{-3}$ dynes. This equals approximately $2\times10^{-8}$ Newtons, which is that force required of the gravity wave to propitiate the vibration of melatonin and neurotransmitter molecules. When the mass is $4\times10^{-22}$ grams and the biological length that is resonated is that of a cell (in the biological system). With a cell approximately $6\times10^{-4}$ cm (l), we get approximately $6\times10^2$ dynes ($6\times10^{-3}$ Newtons). This is the force required to vibrate neurotransmitter or melatonin molecules in a single cell. That force is $3\times10^5$ times more powerful than the force required to vibrate through a human length. This shows a subtle resonance variation in force to jiggle a nucleotide molecule from human length to cell length. The difference in (F) is a factor of approximately $3\times10^5$, which is approximately the differential of $3\times10^5$ V/cm across the cell membrane. The amplification is accomplished by the larger organism. In other words, the force required to jiggle a particle in a cell is greater than a harmonic force to jiggle the same particle in a multicellular animal. The vibration wave is enhanced by the longer organism. In string theory, this is the reason for the existence of superstrings. The enhancement capability of the human body of propagating a gravity wave is about $3\times10^5$ times greater than the capability of the single cell.

Jacobson Resonance, in terms of ($mc^2$) divided by (l) demonstrates a force as the standard archetype. It is important to note that Jacobson Resonance works in MKS and CGS when $qvB=mc^2/l$. The induced electromotive force is a force of electrical pressure through ordinary matter or EM field. The gravity wave is a force which is defined as qvB when the constant of proportionality (q) is equal to unity. In Jacobson Resonance, the force of a gravitational wave is defined in the same way as force is defined. (v) is the velocity of the mass contained by (l) in a particular coordinate system. The charge appertains to mass in ion cyclotron resonance (ICR) but not Jacobson Resonance. In Jacobson Resonance, the mass may contain ions, but we view only the mass as traveling at the inertial velocity (v) within the conductor (l). The amount of ions in the mass is irrelevant. (q) is relevant only insofar as it relates to the fundamental unit of coulomb, the harmonic of ultimate unit charge, the charge of the electron. In addition to neurotransmitter or physiologically active amine molecules being vibrated in the cell, the stronger harmonic will also vibrate viruses or large genomic masses, denoted as genomic magnetic domains. Regions having different ground state configurations separated locally by an interface of infinite energy are called solitons, and are vibrational waves of lossless character. This is why milligauss fields are about $10^5$ times stronger than a typical physiologic magnetic field. A typical physiologic magnetic field includes a range in general from a microgauss to a picogauss.

Picotesla magnetic fields can be seen in Table I to be associated with various mass resonances, from neurotransmitters to oncogenes and homeoboxes. The fundamental prediction of Jacobson Resonance in medicine is that $10^{-8}$ gauss magnetic fields can be sourced extrinsically to treat human disease. Recent data is presented in Table I, below.

TABLE 1

Critical biological frequency associations in ion cyclotron resonance and Jacobson resonance are shown. Magnitudes are presented with a general list of targets.

| $f_{icr}$ | $q/2\pi m$(ion) | (B)flux density | $m_{jr}$ (target mass) |
|---|---|---|---|
| 1.1 Hz | $2.8 \times 10^7$ $Cg^{-1}$ | $3.9 \times 10^{-8}$ G | NGF, melatonin, PDGF oncogene associated protein (leukemia) physiologically active amines (dopamine, epi, norepi, GABA, serotonin histamine) enzymes. |
| 16 Hz | electron | $5.7 \times 10^{-7}$ G maximum heart rate | oncogenes, homeoboxes immunoglobulins. |
| 60 Hz | calcium (760 $Cg^{-1}$) | 80 milligauss | oncogenes and homeoboxes when l is cellular. |
| 60 Hz | proton $1.5 \times 10^4$ $Cg^{-1}$ | 4 milligauss | water molecular when l is cellular and v equals earth's rotational velocity, small antigen (4 kD). |
| $1.4 \times 10^7$ Hz | electron | 0.5 G (geomag) | enzymes when Vorb, l is viral; and Vrot when l is bacterial $m_{jr}$ is circulating immuno-globulins, oncogenes and homeoboxes, when l is viral and V is rotational then $m_{jr}$ can be hormones and neurotransmitters. |
| $7.5 \times 10^3$ Hz | proton | 0.5 G | same as above |
| $1.4 \times 10^5$ Hz | electron | 4 milligauss | water molecular, enzymes when l is that of a human the target masses may be entire genomes (hazardous*). |

*as a general statement, radio frequencies and milligauss fields can be hazardous to health. Safe physiologic range of flux density is a microgauss to a picogauss. Biological frequencies up to 100 Hz with physiologic magnetic fields may be utilized in magnetotherepy.

| 60 Hz | electron | $2 \times 10^{-6}$ G outer space | enzymes, trophic factors, large antibodies. |

Magnetic profiles of organs such as brain and hear as well as aggregations of cells withdrawn from the body should be determined. We may establish changes in trace metals, quantities in cells and tissues which are critical in the determination of normal genetic information transfer. When the wrong trace metals are present or when there is an excess of trace metals which are ordinarily necessary for normal genetic informationtransfer, crosslinking may occur producing genetic mistakes. Such errors result in structural deformations of DNA, RNA and proteins that are responsible for the structure and function of cells.

| 1.4 Hz | electron | $5 \times 10^{-8}$ G | melatonin when Vrot and l is human. |
| $2 \times 10^{-2}$ Hz | electron | $7 \times 10^{-10}$ G | melatonin when Vorb and l is human. |

It has been noted that multiple point source production of 5–25 pT MF about the posterior portion of the corpus callosum shows the BiotSavart law, pineal hypothalmic tract mediation is a fact to consider.

| $2 \times 10^{-3}$ Hz | electron | $6 \times 10^{-11}$ G | water (18D); l = human v = orbital. |
| $2.1 \times 10^{-3}$ Hz | electron | $7 \times 10^{-10}$ G | neurotransmitters, hormones, melatonin (123D—400D), l = human, v = orbital. |
| $2 \times 10^{-1}$ Hz | electron | $7 \times 10^{-9}$ G | small antigens, l = human, v = orbital. |

TABLE 1-continued

Critical biological frequency associations in ion cyclotron resonance and Jacobson resonance are shown. Magnitudes are presented with a general list of targets.

| $f_{icr}$ | $q/2\pi m$(ion) | (B)flux density | $m_{jr}$ (target mass) |
|---|---|---|---|
| 2.1 Hz | electron | $7 \times 10^{-8}$ G | enzymes, trophic factors 13.5KD–68KD. |
| 9 Hz | electron | $3 \times 10^{-7}$ G | homeoboxes, oncogenes, 90KD–300KD |

Note: When the velocity is the earth's rotational, then the flux densities are 65 times greater than with the orbital earth velocity.

| | | | |
|---|---|---|---|
| 16 Hz | calcium | 20 milligauss | enzymes, trophic factors, whole viruses $10^{-17}$ g– $10^{-18}$ g when l = human child. |

Note: Jacobson Resonance shows at 4 milligauss; when the length of the biological system is human birth size about 50 cm and the inertial velocity is the earth's rotational, the target mass is viral. When B is 2 milligauss, the biological length is 100 cm (3 ft. 4 inches) a child's height. Furthermore, at 4 milligauss, the target mass is the water molecular when the inertial velocity is the earth's rotational and the biological length is that of a small cell, about $2 \times 10^{-4}$ cm. These correlations show that milligauss fields vibrate critical molecules in cells and can lead to structural deformations of said molecules. This occurs though there are some therapeutic aspects to such fields.

| | | | |
|---|---|---|---|
| 0.7 Hz | electron | $2.5 \times 10^{-8}$ G | $m_{jr}$ = electron $9.11 \times 10^{-28}$ g when Vrot and l = cellular $7 \times 10^{-4}$ cm (RBC). |
| $4 \times 10^{-8}$ Hz | electron | $1.5 \times 10^{-15}$ G | electron, Vorb, l = human. |
| $1.1 \times 10^{-4}$ Hz | electron | $4 \times 10^{-10}$ G | electron, Vorb, l = cellular. |
| 0.75 Hz | proton | $5 \times 10^{-5}$ G | proton, Vrot, l = cellular. |
| 19 Hz | electron | $8 \times 10^{-7}$ G | proton, Vorb, l = cellular. |
| $8 \times 10^{-5}$ Hz | electron | $3 \times 10^{-12}$ G | proton, Vorb, l = human. |

Note: When the biological length is cellular, the target mass should be no greater than a proton to insure safety.

| | | | |
|---|---|---|---|
| 30 Hz | proton | 2 milligauss | small antigen 1.4 kD Vorb, l = cellular. |
| 45 Hz | proton | 3 milligauss | Vrot, l = cellular, calcium, $H_2O$ |
| 2.3 Hz | $Ca^{++}$(760 $Cg^{-1}$) | 3 milligauss | viral or genomic domain, l = 90 cm = 3 ft.; Vrot. |
| 1.5 Hz | $Ca^{++}$ | 2 milligauss | viral mass, Vrot, l = human child (60 cm). |

Note: When milligauss fields are associated with Vrot, and l = human, viral particles are vibrated. Milligauss fields with $q/2\pi m$ of the electron can be associated with radio frequencies. Therefore, mG fields with RF can jiggle viral and genomic domains to produce recrystallization.

As shown in Table 1, the values for q in the formula $f_c = qB/(2\pi m)$ vary, e.g., q=1(unity) or q=any number of charges of ions ($Ca^{++}$, $K^+$, $Mg^{++}$, etc.) or charges of species (electrons, protons, etc.). This gives a frequency range of DC to $10^{14}$ Hz.

Table 2 shows further examples of flux density, frequency and targets. l=human, and v=orbital velocity.

TABLE 2

| $f_o$ | B | target |
|---|---|---|
| $2.1 \times 10^{-2}$ Hz | $7 \times 10^{-10}$ G | hormone neurotransmitters, melatonin, 240–400 D. |
| 2.1 Hz | $7 \times 10^{-8}$ G | enzymes, trophic factors, approx. 13.5 KD–68 KD. |
| $3 \times 10^{-8}$ – $3 \times 10^{-9}$ Hz | $10^{-15}$ – $10^{-16}$ G | electrons |
| 9 Hz | $3 \times 10^{-7}$ G | homeoboxes, oncogenes, approx. 90 KD–300 KD. |
| $3 \times 10^{-13}$ Hz | approx. $10^{-20}$ G | neutrinos |
| $2 \times 10^{-3}$ Hz | approx. $6 \times 10^{-11}$ G | water and trace metals (18 D). |
| $9 \times 10^{-5}$ – $3 \times 10^{-7}$ Hz | $3 \times 10^{-12}$ – $10^{-14}$ G | protons, deuterons, tritons, muons |
| $2 \times 10^{-1}$ Hz | $7 \times 10^{-9}$ G | small antigens |

Note:
(B) for rotational velocity (Vrot) = 65 times greater than (B) for orbital velocity (Vorb)

Jacobson Resonance works in terms of solving for qvB Force. This force is also manifested by the vibrational wave which passes through the spines of proteins through plasma membranes. In dark solitons, the membrane goes dark as the refractive index changes in accordance with permitivity changes. The permitivity of the tissue changes as the structure is vibrated by the gravity wave. Landau levels adjust as Fermi energies change, quasi particles are popped out of the quantum vacuum, Hall conductivity plateaus show fractional multiples of $e^2/h$.

It has been demonstrated that cells are affected in a variety of ways with fields as low as $8 \times 10^{31\ 4}$ gauss. It has been further demonstrated that oncogenic expression is related to environmental magnetic fields hundreds of times weaker than the earth's steady magnetic field called the geomagnetic field. Additionally, epidemiological data shows a definitive correlation between childhood leukemia and magnetic fields on a three-level scale: $-0.09, 0.10$–$0.19, 0.20$ -$\mu$T; which sets a cut off point at $9 \times 10^{-4}$ gauss.

The following is the foundation of the mathematical perspective. Jacobson resonance is defined as $$mc^2 = Bvlq, \quad (1)$$

when B, v and l are mutually perpendicular.

Equation (1) is a scalar form and a more general form may be expressed as $$mc^2 = (q\vec{v} \times \vec{B})l \quad (2)$$

$$mc^2 = q(v\ B\ \sin \theta)l \quad (3)$$

Equation (1) is the special case of equations (2) and (3) where the angle $\theta$ is $\pi/2$. In biological terms, (l) is the length of the organism. The applied physical meaning is discussed later. (L) represents a general term for distance.

The units of equations (1) through (3) check out as follows:

$$M L^2 T^{-2} = (MQ^{-1}T^{-1})(LT^{-1})L \, Q \qquad (4)$$

The expression for Zeeman Resonance is:

$$E = mc^2 = g_e \beta_e Bc \qquad (5)$$

The Bohr magneton $\beta_e = (q^2 n)/(2mc) = (q^2 n)/(4\pi mc)$ $$\text{Now, } \frac{q^2 \hbar}{4\pi mc} = \frac{qmc^2 t}{4\pi mc} = \frac{qct}{4\pi} = \frac{qL}{4\pi} = \frac{qr}{2} \qquad (6)$$

$$\text{Thus, } g_e \beta_e Bc = g_e \frac{Bcrq}{2} = mc^2 \qquad (7)$$

$$\text{Also, } E = mc^2 = 2qmc^2 \frac{t}{4\pi mc} Bc \qquad (8)$$

Dividing both sides by $mc^2$ and by t, we get the expression, $$\frac{1}{t} = \frac{qB}{4\pi m} = f \qquad (9)$$

precisely the expression for cyclotron resonance. Additionally, $$g_e = 2.002322,$$

and $$E = Bcrq \qquad (10)$$

from Equation (7).
Also, cyclotron resonance may be expressed as $$\frac{v}{r} = \frac{qB}{m} \qquad (11)$$

When $v_{max}$ of the ion is c, we may write $$\frac{c}{r} = \frac{qB}{m} \qquad (12)$$

$$mc = qrB \qquad (13)$$

Multiplying both sides of equation (13) by c, we get $$mc^2 = Bcrq$$

We note that Jacobson Resonance is a general expression of Zeeman and cyclotron resonance when $v_{max}$ of the ion considered in the system is the speed of light (c) and r=l.

It must be noted that Zeeman resonance and cyclotron resonance are equivalent to Jacobson Resonance when $v_{max}$=c and r=l. It must be particularly noted that the general expression $mc^2$=Bvlq describes a system wherein the g factor is electronic, $g_e$=2. This distinction may be explained with the utilization of string theory.

In string theory, the manifestation of a particle depends upon its internal state of vibration and its linear extension in space-time. Although the term linear refers to curvilinear to geodetic line, the perception of a straight line is fundamentally relativistic. More specifically, the arc of a semi-circle is a string with total length approximately 6.28 or $\pi r$, when r=2. When the string is closed into a full loop, the diameter is 2. The radius of the arc of the semi-circle having a length of 6.28 is 2, wherein the diameter of the closed loop is equal to 2. Thus r=l, where l is the extension seen cross-sectionally in two dimensions. The diameter of the open arc of 6.28 is equal to 4. The electronic g factor describes a string manifested as an electron point mass when the loop is closed. The nuclear g factor describes a string manifested as a proton as the string is open into the arc of the semi-circle, and as this arc is further extended linearly, a perceiver looking at the string from a two-dimensional planar angle cross-sectionally sees a string approximately 5.6. This is because the arc string is open somewhat in between a totally extended linear state and the fundamental state of a semi-circular arc wherein the diameter would be 4. Thus, string theory explains the necessity for the variation of the electronic g factor to the nuclear g factor; explained as the same string manifesting itself as two different fundamental particles, dependent upon the extension in space-time regulated by the internal state of vibration.

The following is an example application of Jacobson Resonance and cyclotron resonance. First we select a particular target thought to be critically important for a process. Now, let us take for example nerve growth factor. Mass (m)=13, 250 daltons, the mass of a single protein of two identical proteins that comprise the NGF molecule. Mass (m) in CGS is $2.213 \times 10^{-20}$ grams. (c) is the speed of light at $3 \times 10^{10}$ cm sec$^{-1}$, (v) is the orbital velocity of the earth at $3 \times 10^6$ cm sec$^{-1}$. Length (l) is the height of the patient at five feet, eight inches or $1.7 \times 10^2$ cm. The flux density (B) is solved as follows.

$$mc^2 = Bvlq$$

$(2.213 \times 10^{-20} \text{ g})(9 \times 10^{20} \text{ cm sec}^{-2}) = (B)(3 \times 10^6 \text{ cm sec}^{-1})(1.7 \times 10^2 \text{ cm})(q).$ When q=unity, $$B = 3.9 \times 10^{-8} \text{ gauss} \qquad (15)$$

Now, $q/(2\pi m)$ for the electron is $2.79874 \times 10^7$ C g$^{-1}$. Substituting in $f_c = qB/(2\pi m)$, results in $$f_c = (2.79874 \times 10^7 \, C \, g^{-1})(3.9 \times 10^{-8} \text{ gauss})$$

Accordingly, $f_c$=1.09 Hz (65.4 beats min$^{-1}$)

Note the fundamental correlation of NGF to delta brain wave frequency, while keeping in mind that CNS and PNS nerve cells that have been demonstrated to respond to NGF include the sensory and sympathetic which regulate involuntary functions such as the beating of the heart and blood flow.

In general terms, Jacobson Resonance says, $$\frac{c^2}{l} = \frac{qB}{m} \qquad (16)$$

$$\frac{L^2 T^{-2m}}{L^2 T^{-1}} = \frac{qB}{m} = f \qquad (17)$$

When $(q)$=unity, $$\frac{3.9 \times 10^{-8} \text{ gauss} \times (l)}{2.2 \times 10^{-20} \text{ grams}} = 1.76 \times 10^{12} \text{ Hz} \qquad (18)$$

Additionally, $$f = \frac{2.4 \times 10^{-6} \text{ gauss}(l)}{2.2 \times 10^{-20} \text{ g}} = 1.13 \times 10^{14} \text{ Hz} \tag{19}$$

$2.4 \times 10^{-6}$ gauss is obtained when v=earth's rotational velocity and $m = 2.2 \times 10^{-20}$ g.

Dividing $1.13 \times 10^{14}$ Hz by $2\pi$ gives, $1.8 \times 10^{13}$ Hz.

Finally, in Jacobson Resonance we see a variation in physiological organismic or molecular vibrational frequency from about $2.8 \times 10^{11}$ Hz to about $1.13 \times 10^{14}$ Hz.

From the example of Equation (18), we note that when $m = 2.2 \times 10^{-20}$ grams (NGF), $v = 3 \times 10^6$ cm sec$^{-1}$ (orbital velocity of the earth), $c^2 = 9 \times 10^{20}$ cm$^2$ sec$^{-2}$ (speed of light squared) and $l = 1.7 \times 10^2$ cm (average human length fully extended) then $B = 3.9 \times 10^{-8}$ gauss (a physiologic flux density), $2.4 \times 10^{-6}$ gauss is a typical space flux density cutting biological systems incessantly and is a physiological safe maximum.

Hydrogen bonds (HB) in genes, which play a role in mutation, are to be found in proteins and nucleic acids. According to the biophysics literature, the nature of HB between two electronegative atoms is described as essentially electrostatic. In this particular bond, one positively charged particle (H$^+$) is mutually attracted by two electronegative atoms, separated by 1–2 nm, so the phenomenon itself gets a very high frequency oscillating character. The frequency of HB oscillation varies; nevertheless it belongs to the wide spectral region of infrared, between $10^{14}$ and $10^{11}$ Hz. More particularly, as far as HB of proteins and DNA is concerned, their oscillation frequency has been estimated in the order of $10^{11}$ Hz for DNA and $10^{12}$ Hz for some proteins (hemoglobin, lysozima, keratins, poli-L-alanin and others). Therefore, we can look at hydrogen bonds in DNA and proteins as at sources of electromagnetic radiation, ranging from millimeter waves ($10^{11}$ Hz) to far infrared ($10^{12}$ Hz).

Chains of hydrogen bonds are present in alpha-helices, beta-sheets of proteins and in nucleic acids wherein they connect complementary base pairs. The maximal stability of the HB is reached when the four atoms NHOC lie on the same axis; but the bonds can also be stretched and compressed, so DNA and proteins acquire piezoelectric properties and modify their electric states when they interact with physical energies of various type: mechanical compression and tension, ultrasound, alternating electromagnetic fields. Intra-cellular and extracellular HB behave like energy transduction piezoelectric centers whose biophysical properties probably depend on their length. As HB undergo stretching and compression, their oscillation frequency will correspondingly change. A "musical" model has been devised in which HB are compared to the strings of a string instrument; the harp. On the length, number and cooperation of 'strings' (small and large hydrogen-harps) will depend the frequency, intensity and quality of 'sound' (i.e. electromagnetic emission). Jacobson Resonance presents a physico-mathematical account for the hydrogen-harps model. This can be utilized to explain some essential moments of proteins and DNA function on the basis of its logical connection with Frohlich's theory of coherent excitations. It also helps the understanding of the second genetic code mechanisms.

Indeed, we see resonances based in time, mass and distance. We note that biological amplification of ELF, low intensity photon energy fields by a factor of $10^{12}$, through high molecular vibrational frequencies, accounts for the bigger kT consideration. The necessary connection of solitary vibrational waves, ethereal waves and heating may be unified with application of Jacobson Resonance.

It has been thought that since the duration of a typical collision in a molecular fluid is fixed at a given temperature and pressure, the field frequency determines whether there is a relaxation or resonance spectrum. There is no compelling evidence, physicists have maintained, for resonant absorption in ordinary molecular fluids below about 3,000 gigahertz. Of course the data clearly shows that there does occur resonant phenomena throughout the galaxy of frequency and amplitude combinations in biological systems. The affectation generally involves an integration over time to produce manifestation of amplification of weak signal transductions. Yet, Jacobson Resonance shows the possibility of spontaneous structural conversions through transmutation of dark matter. Connecting ethereal deformations or particulate group velocity linkages with typical heating effects based in very high molecular vibrational frequencies of ordinary matter already derived of Jacobson Resonance, there must be spontaneous lossless dark soliton phenomena. The portion of receptor proteins which lie in plasma membranes, are comprised of a helix of about six turns, and are composed entirely of hydrophobic amino acids, incapable of hydrogen bonding or ionic conduction; yet mediate the rapid transfer of ions.

Conversion of electromagnetic oscillations to mechanical vibrations and vice versa; i.e., piezoelectricity, in this regard, is critically important and is related to the fractional quantum Hall effect. Herein, quasi-particles are popped out of a quantum vacuum to accommodate adjustments in the metric of space-time (the four dimensional manifold) due to the continued existence of smaller perturbations in intensity and frequency, relative to the bigger heating and pressure components of the strong and weak nuclear forces of ordinary matter. Landau levels reorient and Fermi energies rise to account for the subtle pressure of weak, low intensity fields on the real manifold. Thus, solitary solutions to non-linear relativistic field problems yield the necessary existence of spontaneous productions of vibrational waves which are apparently lossless in character. Indeed, a soliton is fibrillation of the four dimensional manifold. The arrow of time and the inflationary cosmological constant can be explained in this regard. The inflection is based in the mutual repulsion of ponderable bodies which compete for the same reality within the manifold and point to a negative quantum gravity as a magnetic vector potential.

When E is the photon energy, h is the Planck's constant and v is the frequency of the radiation:

$$E = h\nu \tag{20}$$

When f=16 Hz, an important Ca$^{++}$ window, then $$E = (6.626 \times 10^{-34} \, J \text{ sec})(16 \text{ Hz}) = 1.06 \times 10^{-32} \text{ Joules} \tag{21}$$

Now, k is a constant equal to R/L, where R is the universal gas constant and

L is the Avogardro constant. It has the value $1.380622 \times 10^{-23}$ J K$^{-1}$. When K is body temperature, 370° C., or 310° Kelvin, then $$kT = 1.380622 \times 10^{-23} \text{ J k}^{-1} \cdot 310° \text{ K.} \tag{22}$$

$$= 4.28 \times 10^{-21} \text{ Joules}$$

Therefore, dividing equation (22) by equation (21), we get $$\frac{4.28 \times 10^{21} \text{ J}}{1.06 \times 10^{-32} \text{ J}} = 4.04 \times 10^{11} \quad (23)$$

The molecular vibrational frequency of the DNA hydrogen bonds which connect the nucleotides is about $4.04 \times 10^{11}$ Hz. Every body (A) which is even infinitesimally affected by another force from body (B) will relate that effect to another body (C). If body (A) is moving with frequency ($f_1$) intensity ($I_1$) and directionality ($D_1$) while body (B) maintains frequency ($f_2$), intensity ($I_2$) and directionality ($D_2$) all affectations will produce effects mechanically and electromagnetically transmittable by body (A) to body (C) and ($f_1$)($I_1$) and ($D_1$) will all be influenced and reoriented within the four-dimensional manifold. Thus DNA (HB) will amplify week signals extrinsically sourced whether they are mechanical, electromagnetic or gravitational.

Outer space magnetic fields interact inertially with the human body. A weak magnetic field on the order of magnitude $10^{-6}$ gauss permeates outer space, while its extension and degree of order are of course uncertain. Yet we may write the following relations involving fundamental mass harmonics which are gauge interactions, no doubt occurring within the scope and breath of our local solar system.

$$E = (\text{mass of proton, } m)(c^2) \quad (24)$$
$$= (2.7 \times 10^{-24} \text{ g})(9 \times 10^{20} \text{ cm}^2/\text{s}^2)$$
$$= (10^{-6} \text{ gauss})(3 \times 10^6 \text{ cm})(7.7 \times 10^{-4} \text{ cm})$$

(B)flux density of · orbital · Average diameter
outer space   velocity   of RBC
              of earth $$(5 \times 10^{-19} \text{ g}) (9 \times 10^{20} \text{ cm}^2/\text{s}^2) = \quad (25)$$
$$= \text{mass of}$$
oncogenic magnetic
domain homeobox,
immunoglobulins ($10^{-6}$ gauss)  ($3 \times 10^6$ cm/s)  ($1.5 \times 10^2$ cm)
Flux density   Orbital      = Length of
(B) of outer   velocity of   human
space          the earth $$f_c = \frac{qB}{2\pi m} \text{ wherein } \frac{q}{2\pi m} \text{ of } e^- \text{ is about } 2.78 \times 10^7 \frac{\text{coul}}{\text{g}}$$

Therefore, $$f_c = 60 \text{ Hz} = (2.78 \times 10^7 \text{ coul/g}) \ (2.2 \times 10^{-6} \text{ gauss}) \quad (26)$$
Gyromagnetic       (B) of outer space
ratio of $e^-$ This delineates one reason why 60 Hz and 72 Hz bioeffect windows have been observed with non-ionizing EM, exogenously sourced radiation. Of course there are a multiplicity of interactions which are mid-range biological frequency affectations.

Considering cyclotron resonance frequency 72 Hz as it may relate to biological systems, we note that $q/(2\pi m)$ of proton is $1.5 \times 10^{-4}$ C $g^{-1}$ 72 Hz    = $(1.5 \times 10^4$ C $g^{-1})$ $(4.8 \times 10^{-3}$ gauss$)$  (27)
Biological   Proton         cellular flux
frequency    gyromagnetic   density
window       ratio Applying $4 \times 10^{-3}$ gauss to a Jacobson Resonance system:

$$(2 \times 10^{-22} \text{ g}) \ (9 \times 10^{20} \text{ cm}^2 \text{ sec}^{-2}) = \quad (28)$$
(m)           ($c^2$)
neurotransmitter
and hormone
mass $(4.8 \times 10^{-3}$ G$)$  $(4.8 \times 10^4$ cm sec$^{-1})$  $(8 \times 10^{-4}$ cm$)$
(B)              (v)              (l)
                 rotational       REC
                 velocity of earth diameter Patient orientation may be an important factor in treatment. Reports have come from the Institute of MagnetoBiology in Madras that patients oriented in an east-west position, while immersed in magnetic fields improved electrophysiological parameters (EEG, ECG, respiration, peripheral blood flow) neurochemistry and biochemistry, while north-south orientations denigrated the same.

Magnetic fields of 0.1 Hz at +/−300 nT were impressed. A number of diseases were reported to be successfully treated; such as rheumatoid arthritis, osteoarthritis, cervical spondylosis, lumbar spondyloses with sciatica, migraine, festering wounds, diabetic ulcers, malunion of fractures, depression and even chronic alcoholism. Patients were treated for thirty minutes for thirty days.

More specifically, in experiments with the head toward the north, sudden inhibition of electrical activity of the brain was noted with severe vaso-constriction of the peripheral blood vessels. Subjects were restless and there was mental confusion, whereas in the east orientation, subjects were very calm. In the east orientation, there was augmentation of brain electrical activity; especially in the alpha and beta rhythms, indicating a state of restful alertness. In the east orientation of the patient, it was noted further that the polygraph record indicated profound vasodilation of the peripheral vessels showing increased blood flow; hence the oxygen and nutrient supply to affected regions. Sugar content of the blood was increased; plasma cortisol was also raised in the north orientation. There was no significant change in east orientation. Cholesterol increased in the north orientation and remained normal in the east orientation.

Now, when $\pi/2$ is the angle between B, v and l, maximum effect is achieved. In the Madras study, orientation of the magnetic flux lines was north-south, essentially parallel to the geomagnetic field lines of force. Therefore, normal interaction of patients with the geomagnetic field was based in the east orientation, while the benefit or harm from the experimentally imposed field was also maximized. The north orientation denigrated the effects of the geomagnetic field and the experimental.

It seems reasonable to presume that maximum effect of geomagnetic and therapeutic signals can be achieved when the therapeutic signal is parallel to the geomagnetic, and when the long axis of the patient is perpendicular to both the north-south magnetic lines of force and the orbital direction of the earth.

Thus, if a patient is standing erect on the earth, maximum effect is achieved in between sunrise and sunset. If the patient is in a supine position with the head somewhat elevated while oriented east-west, maximum effect of the therapeutic signal will be achieved at sunrise and sunset.

It must be pointed out that the precession of equinoxes are not permanent, the axis of the earth makes an angle of about 23 degrees, 27 minutes with the perpendicular, the orbit of the earth is shaped like an ellipse with the sun as one of its foci, and the curve traced by the earth's axis is not a smooth circle, but has small waves known as mutation. The true motion of the earth is a combination of the precession and the nodding motion (nodding motion of the earth's axis about the mean position of 23 degrees, 27 minutes). The period of one such complete wave length is nineteen ears, and the amplitude is nine seconds of angle, which may be correlable to activity of the sun as well as to the gravitational effect of our moon. These and other astronomical considerations must be weighed in clinical terms.

Experimental, clinical and epidemiological data has sent us mixed signals concerning the bioeffects from milligauss fields of extremely low frequency. Interestingly, even PEMFs (pulsed electromagnetic fields) as great as 20 gauss have been in clinical use for years to enhance osteochongrogenesis, without discernment of any deleterious side effects. Experiments by a host of researchers nevertheless have documented that fields a little stronger than the geomagnetic at biological frequencies have enhanced oncogene transcription (e.g., c-myc and c-fos) influenced critical enzyme activity (e.g., adenylate cyclase, protein kinase c, ornithine decarboxylese) showing a maximum effect at 16 Hz. This contributed to actions of cancer promoters at gap junction levels promoting epigenetic or non-genotoxic carcinogenicity. Indeed, cell contact and intercellular communication is an important factor in determining cellular response to EMFs. Transcripts of genes involved in metabolic activity, development and cell division have been shown to increase when exposed to elf EM field, applied AC current or induced AC current. Examples of these are: histone H2B, actin, tubulins in human and dipteran cells URA3 in yeast and several homeobox genes in Drosophila including Ubx. Recent data on protein synthesis patterns show elevated synthesis of heat shock protein hsp 70 kD in samples exposed either to EM fields or sudden elevated temperatures. RNA samples were retested from exposed and control samples and transcript levels were measured for the heat shock gene hsp 70. Frequencies and field strengths used were: 60 Hz, 8 $\mu$T and 60 Hz, 80 $\mu$T. An increase in transcript levels for the heat shock gene hsp 70 was present. Families of heat shock genes, found in all organisms examined, have been shown to respond to a wide variety of stresses in addition to sudden elevated temperature (e.g., oxidative agents, viral infections, cell cycle arrest, and nutritional starvation). Although stress proteins have been shown to have essential roles in normal biosynthetic events in the cells, the deregulation of stress gene expression and the aberrant expression of the proteins coded by these genes has been detected in a number of diseases. The c-myc protein is known to bind to the human hsp 70 promotor region and is involved in the regulation of hsp gene. Calcium, second messengers and kineses which may be involved in the signal transduction pathway by which EM fields interact with cells during exposure are also involved in the activation of transcription of the hsp 70 gene.

The main point of Jacobson Resonance here is that signals stronger than the geomagnetic are non-physiologic and only acute exposure should be considered for clinical purposes. Furthermore, milligauss signals are fundamentally attuned in cellular resonances and are not to be trusted in the treatment of humans. Physical ordering of a small portion of a biological system does not mean that biological order will result, nor does partial physical disorder necessarily produce biological disorder. In a highly non-linear, non-equilibrium system like the human organism, it is maintained that only signals weaker than $10^{-6}$ gauss can be presupposed as physiologic for clinical purposes because whole body resonance dictates this conclusion. The multiplicity of target mass, frequency and extension resonances requires this critical decision about milligauss fields. Sample calculations which show the importance of geomagnetic fields, target mass and cellular resonances in conjunction with critical frequencies with varying potentials follow.

$$(4 \times 10^{-20} \text{ g})(9 \times 10^{20} \text{ cm}^2 \text{ sec}^{-2}) = \tag{29}$$
$$(0.5 \text{ G})(3 \times 10^6 \text{ cm sec}^{-1})(2.4 \times 10^{-5} \text{ cm})$$

enzyme, growth · $(c^2)$ =
factor mass($m$)

$$\begin{array}{ccc} \text{geomagnetic} & \text{earth's orbital} & \text{viral} \\ \text{field}(B) & \text{velocity}(v) & \text{length}(l) \end{array}$$

The geomagnetic field is attuned to viral and cellular length in terms of relating gravitational potential of critical molecules and EM fields in duel resonance, according to inertial electromagnetic induction systems.

$$(4 \times 10^{-20} \text{ g})(9 \times 10^{20} \text{ cm}^2 \text{ sec}^2) = \tag{30}$$
$$(0.5 \text{ G})(4.8 \times 10^4 \text{ cm sec}^{-1})(7 \times 10^{-4} \text{ cm})$$

enzyme, growth · $(c^2)$ =
factor($m$)

$$\begin{array}{cccc} \text{geomagnetic} & \text{earth's} & & \text{RBC} \\ \text{field}(B) & \text{rotational} & & \text{diameter} \\ & \text{velocity}(v) & & \text{cellular length}(l) \end{array}$$

We see how our terrestrial steady magnetic field has been critical to the evolution of living systems as known to be.

$$(16 \text{ Hz}) = (7.6 \times 10^2 \text{ C g}^{-1})(2 \times 10^{-2} \text{ G}) \tag{31}$$

$$\begin{array}{ccc} \text{Ca++} & \text{gyromagnetic} & \text{20 milligauss} \\ \text{window} & \text{ratio for} & \text{cellular} \\ \text{frequency} & \text{Ca++} & \text{resonance} \end{array}$$

Studies have been conducted in the city of Madras in India by the Institute of Magnetobiology. Approximately 3 milligauss fields at 0.1 Hz used in the Madras clinical trials are possibly likened to epidemiological studies associating childhood cancer with chronic exposure to 60 Hz electrical power distribution systems, even though frequency was much lower.

$$(4 \times 10^{-20} \text{ g})(9 \times 10^{20} \text{ cm}^2 \text{ sec}^{-2}) = \tag{32}$$
$$(2 \times 10^{-2} \text{ G})(3 \times 10^6 \text{ cm sec}^{-1})(6 \times 10^{-4} \text{ cm})$$

enzyme mass · $(c^2)$ =
($m$)

$$\begin{array}{ccc} \text{(20 milligauss)} & \text{orbital earth} & \text{cellular} \\ (B) & \text{velocity}(v) & \text{diameter}(l) \end{array}$$

Household appliances like electric blankets do produce 20 milligauss fields and subject people to prolonged exposure.

$$10^{-1} \text{ Hz} = (7.6 \times 10^2 \text{ C g}^{-1})(1.4 \times 10^{-4} \text{ G}) \quad (33)$$

Madras frequency — associated $B$ field $$(3 \times 10^{-22} \text{ g})(9 \times 10^{20} \text{ cm}^2 \text{ sec}^{-2}) = \quad (34)$$
$$(1.4 \times 10^{-4})(3 \times 10^6 \text{ cm sec}^{-1})(6.3 \times 10^{-4} \text{ cm})$$

epinephrine($m$) · ($c^2$) = ($B$) field associated with · ($v$) · cellular Madras $f$ diameter($l$)

Considering that the Madras amplitude was only about one order of magnitude stronger than that needed for cellular extension resonances and target mass epinephrine, we must wonder about possible local physical disordering which might produce systemic biological disordering with chronic exposure. While 3 milligauss fields at 0.1 Hz are less likely to produce negative clinical effects than 60 Hz 80 $\mu$T fields, the possibility cannot be ignored.

$$60 \text{ Hz} = (7.6 \times 10^2 \text{ C g}^{-1})(7.9 \times 10^{-2} \text{ G}) \quad (35)$$

The range of genes changes in expression of transcripts identified in cells exposed to EM fields include housekeeping genes, and genes involved with regulatory pathways. The latter group is of particular importance. Frequency of initiation of mRNA synthesis depends when DNA elements in gene promotor regions, while control of transcription involves interaction of regulatory protein factors with these elements. Effects on regulatory genes thus provide a means for defining altered activity in cells resulting from EM field exposure. Since flow of information resulting from signal transduction can mediate the induction of transcription factors, effects on regulatory genes are also consistent with findings of alterations in calcium flux in cells exposed to fields. Transcripts for the transcription factors c-myc and c-fos are consistently increased in cells exposed to 60 Hz EM fields at 8 to 80 $\mu$T which is 80 to 800 milligauss. Note the B field in equation (34) which corresponds to calcium interaction at 60 Hz relates 80 milligauss.

$$(1.6 \times 10^{-19} \text{ g})(9 \times 10^{20} \text{ cm}^2 \text{ sec}^{-2}) = \quad (36)$$
$$(8 \times 10^{-2} \text{ G})(3 \times 10^6 \text{ cm sec}^{-1})(6 \times 10^{-4} \text{ cm})$$

oncogene and homeobox mass($m$) · ($c^2$) =

($B$ in gene transcript experiments · (orbital earth velocity, $v$) · (cellular diameter)

It must be pointed out that in whole body resonance when the B field is increased above approximately $5 \times 10^{-6}$ G, large non-specific mass aggregates are mechanically vibrated, and this is potentially carcinogenic with chronic or prolonged stress.

There are a wide variety of stresses to biological systems both intrinsically and extrinsically sourced. It has been discussed that the possibility of an additional circulatory system, the vascular interstitial closed circuit (VICC) which accommodates potential fluctuations from structural deformations and normal physiologic changes to propagate ionic pumps which must adjust charge distribution and densities. Indeed, the biochemical messenger system; e.g., the reticuloendothelial system, must work in conjunction with the VICC and biologically closed electric circuits (BCEC) in order to maintain a balance between chemical and electrical signals and fluctuations to produce rhythmic and circadian cycles to perpetuate normal electric and magnetic fields within organ systems. Genes send EM messages and receive EM signals through a complex array of signal transductive coupling mechanisms including the electronuclear force and gravitational force communications. Therefore, we recapitulate the vision of ionic, biochemical, electromagnetic structural reorientations in space and time within biological systems to therein produce in effect what can be called an electromagnetic immune system. The same field intensities and frequencies emitted by epileptic foci to therein attenuate the disorder were fed back to the brain. It is logical to presume that physiologic defense mechanisms produced fields to adjust structural, biochemical and electromagnetic irregularities. The addition of an extrinsic field helped to reinforce the therapeutic signal, which was indeed produced naturally. We see the unification of all four fundamental forces of nature as the promulgator of health and well being. We must further investigate the possibilities and potentialities inherent in the enhancing of the electromagnetic immune system through extrinsic signaling.

The structure and size of viruses must be noted when considering various therapeutic modalities, including both vaccination and recrystallization with extremely low frequency (ELF) and low intensity electromagnetic fields. In this analysis, our focus will ultimately be viruses that can cause human cancers, AIDS, and the approach to use in therapeutics. Viral attack with weak magnetic fields will be explained and vaccination will also be weighed. Recrystallization of viruses, or frank disruption of envelope HIV protein keyed for the CD4 T-lymphocytic cell surface receptors, and prion crystallization through electromagnetic means will be considered. Lymphokines are also targets, as are critical DNA segments, RNA, enzymes, hormones, neurotransmitters and antibodies.

Recapitulating, genes are aggregates of atoms the integrated vector of which has a quantum magnetic moment as do all other important targets; i.e., ponderable bodies of electromagnetic field, matter. Viruses and constituent parts of viruses are targets for resonant mechanical vibrations, as a consequence of electromagnetic interactions. Photon-phonon resonance herein is designated Jacobson Resonance, the equation of which is represented by $mc^2 = Bvlq$. (m) is the mass of the target; e.g., an enzymatic mass is about 26.5 K daltons, the same as NGF (nerve growth factor, a special protein which plays a role in nerve growth; $4 \times 10^{-20}$ grams). ($c^2$) is the speed of light squared, ($9 \times 10^{20}$ cm$^2$ sec$^{-2}$). (B) is the therapeutic flux density; e.g., $6 \times 10^{-8}$ G. (v) is the inertial velocity of (l) the conductive biological system. (v) may be the orbital velocity of the earth, $3 \times 10^6$ cm sec$^{-1}$. (l) is the length of a patient, typically about $2 \times 10^2$ cm. The force carrier of an electromagnetic field travels at speed c, independent of the inertial frame of reference. Interaction is spontaneous according to Special Relativity. We see an energy equivalence between intrinsic energy of a mass and electromagnetic interaction energy, or the energy of the gravity wave 36 ergs is about the intrinsic energy of an enzyme and growth factor according to Einstein. According to the piezoelectric effect, electromagnetic oscillations are turned into the mechanical vibrations of the target, such as an enzyme or viral protein. Vibrations can disrupt a crystalline lattice of a portion of a virus or a whole virus; or, they may help realign biologically disordered structures (depending upon the system of interactions).

Vibrations heat small volumes of matter, and may at melting point decompose organic matter, i.e., viruses decompose before normal proteins. Vibrations can strip away impurities from the outside layer of viral helices and even crystallize this organized matter with characteristic angles. Viral constituents can be shaken out of solution, albeit structurally disrupted.

Thus, it is apparent that there has been provided, in accordance with the invention, a method and apparatus for ameliorating the aging process and the effects thereof utilizing electromagnetic energy. While the invention has been described and illustrated with reference to specific embodiments thereof, it is not intended that the invention be limited to these illustrative embodiments. Those skilled in the art will recognize, after review of the foregoing description, that variations and modifications differing from the illustrative embodiments are possible. It is intended that all such variations and modifications as fall within the spirit and scope of the invention be included within the appended claims.

What is claimed is:

1. A method for ameliorating the aging process and the effects of aging of a patient comprising the steps of:
   (a) generating an electromagnetic field, wherein said field is calculated using a formula of $mc^2 = Bvlq$, wherein m equals a mass of one of a plurality of targets, c equals speed of light, v equals inertial velocity of said mass, l equals length of a conductive body, and q equals unity of charge, to thereby determine a magnetic flux density (B);
   (b) subjecting said patient to said electromagnetic field for a specified period of time; and
   (c) repeating steps (a) and (b) for each of said plurality of targets.

2. The method of claim 1, wherein said step of generating said electromagnetic field comprises applying said field having said flux density in the range of about $10^{-6}$ gauss to about $10^{-20}$ gauss.

3. The method of claim 2, wherein said step of generating said electromagnetic field further comprises a step of calculating a frequency for said electromagnetic field utilizing a formula $f_c = qB/(2\pi m)$, wherein the values for B, and m are equivalent to those calculated in step (a) of claim 1; wherein the value for q is equivalent to unity, a charge of one of a plurality of ions, or a charge of one of a plurality of charged species; and wherein said conductive body is one of said plurality of targets, a complex of said targets or a whole biological system.

4. The method of claim 3, wherein said step of subjecting said patient to said electromagnetic field comprises using a solenoid to which electrical power has been applied.

5. The method of claim 4, wherein said step of subjecting said patient to said electromagnetic field comprises placing said patient horizontally within said solenoid within a tank containing an aqueous solution.

6. The method of claim 4, wherein said step of subjecting said patient to said electromagnetic field comprises placing said patient vertically within said solenoid within a tank containing an aqueous solution.

7. The method of claim 4, wherein said step of subjecting said patient to said electromagnetic field comprises placing said patient horizontally within a tub containing an aqueous solution, said tub surrounded by said solenoid.

8. The method of claim 4, wherein said step of subjecting said patient to said electromagnetic field comprises placing said patient within a pool containing an aqueous solution having said solenoid surrounding a circumference of said pool, wherein said patient walks in a vertical position across said pool.

9. The method of claim 4, wherein said step of subjecting said patient to said electromagnetic field comprises placing said patient within a pool containing an aqueous solution having said solenoid surrounding a circumference of said pool, wherein said patient swims in a horizontal position across said pool.

10. The method of claim 4, wherein said step of subjecting said patient to said electromagnetic field comprises placing said patient within a pool containing an aqueous solution having a pair of opposing magnetic plates on either side of said pool.

11. The method of claim 10, wherein said step of subjecting said patient to said electromagnetic field comprises having said patient walk in a vertical position through said pool.

12. The method of claim 10, wherein said step of subjecting said patient to said electromagnetic field comprises having said patient swim in said aqueous solution in a horizontal position across said pool in a direction substantially perpendicular to a direction flux of said applied electromagnetic field.

13. An apparatus for generating an electromagnetic field for subjecting a patient to ameliorate the aging process and the effects of aging, comprising
   means for generating one of a plurality of electromagnetic fields,
   wherein each of said fields is calculated using a formula $mc^2 = Bvlq$, wherein m equals a mass of one of a plurality of targets, c equals speed of light, v equals inertial velocity of said mass, l equals length of a conductive body, and q equals unity of charge, thereby deriving a magnetic flux density (B); and wherein said conductive body is one of said plurality of targets, a complex of said targets or a whole biological system; and
   wherein a frequency for said electromagnetic field is calculated using a formula $f_c = qB/(2\pi m)$, wherein the values for B and m are equivalent to those calculated above and wherein the value for q is equivalent to unity, a charge of one of a plurality of ions, or a charge of one of a plurality of charged species;
   means for subjecting said patient to each of said electromagnetic fields for a specified period of time.

14. The apparatus of claim 13, wherein said means for generating one of said plurality of fields comprises a solenoid to which electric power has been applied.

15. The apparatus of claim 14, wherein said solenoid is located within a tank containing an aqueous solution, and wherein said patient is placed within said solenoid in a horizontal or vertical position.

16. The apparatus of claim 14, wherein said solenoid surrounds a tub containing an aqueous solution, and wherein said patient is placed within said tub.

17. The apparatus of claim 14, wherein said solenoid surrounds a pool containing an aqueous solution such that said patient swims horizontally or walks vertically across said pool.

18. The apparatus of claim 13, wherein said means for generating said fields comprises opposing plates, having a pool of aqueous solution therebetween.

19. The apparatus of claim 13, wherein said targets from which said mass is obtained for calculating said electromagnetic field are chosen from the group comprising, Peptide hormone trophic factors, nerve growth factor (NGF), platelet derived growth factor (PDGF), interferon, interleukins, protons, electrons, trace metals, proteins, glycoproteins, lipoproteins, structural proteins, enzymatic proteins, water molecules, homeoboxes, or oncogenes.

* * * * *